(12) United States Patent
Tang et al.

(10) Patent No.: US 12,152,010 B2
(45) Date of Patent: Nov. 26, 2024

(54) PREPARATION METHOD FOR PHOTO-ACTIVATABLE AGGREGATION-INDUCED EMISSION PROBE WITH IN-SITU GENERATION CAPABILITY

(71) Applicant: South China University of Technology, Guangzhou (CN)

(72) Inventors: Ben Zhong Tang, Guangzhou (CN); Meng Gao, Guangzhou (CN); Shiwu Li, Guangzhou (CN)

(73) Assignee: SOUTH CHINA UNIVERSITY OF TECHNOLOGY, Guangzhou (CN)

( * ) Notice: Subject to any disclaimer, the term of this patent is extended or adjusted under 35 U.S.C. 154(b) by 1055 days.

(21) Appl. No.: 16/968,426

(22) PCT Filed: Oct. 18, 2018

(86) PCT No.: PCT/CN2018/110815
§ 371 (c)(1),
(2) Date: Aug. 7, 2020

(87) PCT Pub. No.: WO2019/153789
PCT Pub. Date: Aug. 15, 2019

(65) Prior Publication Data
US 2020/0399534 A1    Dec. 24, 2020

(30) Foreign Application Priority Data
Feb. 9, 2018   (CN) .......................... 201810134157.1

(51) Int. Cl.
C07D 277/66    (2006.01)
G01N 21/64     (2006.01)
G01N 33/50     (2006.01)

(52) U.S. Cl.
CPC ....... *C07D 277/66* (2013.01); *G01N 21/6486* (2013.01); *G01N 33/5005* (2013.01)

(58) Field of Classification Search
CPC .......................... C07D 277/64; C07D 277/66
See application file for complete search history.

(56) References Cited

U.S. PATENT DOCUMENTS

2005/0202565 A1    9/2005    Terpetschnig et al.

FOREIGN PATENT DOCUMENTS

| | | | |
|---|---|---|---|
| CN | 104529936 A | 4/2015 |
| CN | 104893711 A | 9/2015 |
| CN | 106279062 A | 1/2017 |
| CN | 107236539 A | 10/2017 |
| CN | 108409685 A | 8/2018 |

OTHER PUBLICATIONS

Li, S. et al. "In situ generation of photoactivatable aggregation induced emission probes for organelle-specific imaging," Chem. Sci., 2018, 9, 5730-5735 and Supporting Information; Published Jun. 1, 2018) (Year: 2018).*
Weekes, A.A. et al. "An efficient synthetic route to biologically relevant 2-phenylbenzothiazoles substituted on the benzothiazole ring," Tetrahedron 67 (2011) 7743-7747 (Year: 2011).*
Yang, X. et al. "Sodium dithionite-promoted synthesis of 2-arylbenzothiazoles by reaction of 2,2'-disulfanediyldianiline with aldehydes in water," Journal of Chemical Research 2009(11): 682-685 (Year: 2009).*
Zhu, N. et al. "New Progress in the Synthesis of 2-Substituent-Benzothiazole Derivatives," Chin. J. Org. Chem. 2013, 33, 1423-1436 (Year: 2013).*
Liu, X. et al. "A Review on Domino Condensation/Cyclization Reactions for the Synthesis of 2-Substituted 1,3-Benzothiazole Derivatives," Eur. J. Org. Chem. 2020, 408-419 (Year: 2020).*
Yamamoto, Koji, et al. "Novel Calcium Antagonists. Synthesis and Structure-activity Relationship Studies of Benzothiazoline Derivatives", Journal of Medicinal Chemistry, vol. 31, No. 5, May 1, 1988.
Donzelli, Alberto, et al. "TilV Complexes of Redox-Active Schiff Bases", European Journal of Inorganic Chemistry, vol. 2012, No. 4, Dec. 13, 2011.

(Continued)

*Primary Examiner* — Jennifer Wecker
*Assistant Examiner* — Michelle Adams
(74) *Attorney, Agent, or Firm* — Hoffmann & Baron, LLP

(57) ABSTRACT

The present invention, belonging to the technical field of biological imaging, discloses a photo-activatable aggregation-induced emission probe with in-situ generation capability, a preparation method therefor and an application thereof. The preparation method is as follows: A bis(2-(2-hydroxybenzylidene)amino)aryl disulfide compound is reacted with thiol to obtain a photo-activatable aggregation-induced emission probe, which has a structure as shown in formula III. In the present invention, the photo-activatable aggregation-induced emission probe is aggregated into a specific organelle, and a 2-(2-hydroxyphenyl)benzothiazole compound having the aggregation-induced emission property is generated through a photo-oxidation reaction. The photo-activatable aggregation-induced emission probe generated in situ of the present invention can effectively overcome the defects of aggregation-induced quenching of traditional fluorescent dyes, and realize organelle-targeted specific photo-activatable fluorescence imaging in living cells, having such advantages as easy preparation, long-term storage, high photo-activation efficiency, large Stokes shift, and strong ability to enter cells.

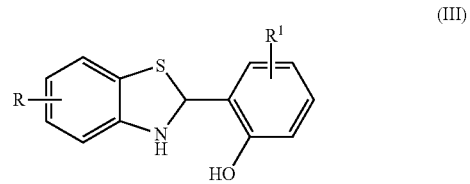

(III)

4 Claims, 11 Drawing Sheets

(56) References Cited

OTHER PUBLICATIONS

Fee, W. W., et al., "Nickel(II) and Copper(II) Complexes with Schiff Base Ligands Containing Remote Substituents", Australian Journal of Chemistry, vol. 26, No. 3, Mar. 31, 1973.
Goetz, Frederick J., "Heterocyclic Tautomerisms. III. An Investigation of the 2-Arylbenzothiazoline-2-(Benzylideneamino)thiophenol Tautomerism. Part3.", Journal of Heterocyclic Chemistry, vol. 5, No. 4, Aug. 31, 1968.
Gu, Xinggui, et al., "Mitochondrion-specific Live-cell Bioprobe Operated in a Fluorescence Turn-on Manner and a Well-designed Photoactivatable Mechanism", Advanced Materials, vol. 27, No. 44, Oct. 7, 2015.
RNú 113864-83-8, Mar. 15, 2020.
RNú 903633-31-8, Mar. 10, 2020.

* cited by examiner

PREPARATION METHOD FOR PHOTO-ACTIVATABLE AGGREGATION-INDUCED EMISSION PROBE WITH IN-SITU GENERATION CAPABILITY

FIELD OF THE INVENTION

The present invention belongs to the technical field of biological imaging, and in particular relates to a photo-activatable aggregation-induced emission probe with in-situ generation capability, a preparation method therefor and an application thereof, especially an application in the field of biological imaging.

BACKGROUND OF THE INVENTION

Photo-activatable fluorescence imaging can achieve high-spatiotemporal-resolution fluorescence imaging through irradiation control, playing an increasingly important role in biomedical research. In order to realize photo-activatable fluorescence imaging, the following problems need to be solved: (1) When traditional fluorescent materials gather in high concentration, their fluorescence will obviously quench themselves; (2) photo-activatable chemical reactions have limited types and low photo-activation efficiency, and may produce toxic by-products; (3) traditional fluorescent materials are difficult to synthesize, and difficult to have photo-responsive groups and biotargeting groups introduced therein; and (4) traditional fluorescent materials cannot be generated in situ and are difficult to store for a long time, which is not conducive to storage, transportation and use.

Aggregation-induced emission materials, as a new generation of fluorescent materials, have the advantages of high photobleaching resistance, high luminous efficiency in aggregated state, large Stokes shift, and low toxicity. These materials can effectively overcome the disadvantages of aggregation quenching luminescence, and are increasingly widely used in the field of biological imaging and detection, particularly suitable for organelle imaging and physiological function exploration. Organelles are subcellular structures in cells with independent functions, including lipid droplets, lysosomes, mitochondria, endoplasmic reticulum, Golgi body, etc., which play an extremely important role in the physiological activities of cells. For example, lipid droplets are an important storage place for lipid molecules and proteins in cells; lysosomes, as "digestive organs" in cells, are responsible for decomposing various exogenous and endogenous macromolecular substances. Compared with fluorescent probes that directly dye organelles, aggregation-induced emission probes with photo-activation capability can be better used to study various physiological functions of organelles. In order to facilitate widespread use in biomedical research, there is an urgent need for a method for directly and efficiently generating photo-activatable aggregation-induced emission probes in situ that is carried out at room temperature based on a simple substrate without any catalyst; this method overcomes the disadvantages of traditional fluorescent materials, such as aggregation quenching luminescence, low photo-activation efficiency, generation of toxic by-products, and difficulty in preparation and storage, and achieves specific photo-activatable imaging and allows physiological function research on organelles.

Contents of the Invention

In order to overcome the disadvantages and shortcomings of the prior art, the primary object of the present invention is to provide a photo-activatable aggregation-induced emission probe with in-situ generation capability. The emission probe of the present invention has the advantages of high in-situ generation efficiency, high photo-activation efficiency, high signal-to-noise ratio, low cytotoxicity, large Stokes shift, strong ability to enter cells, easy storage and use, and the like. The fluorescent probe of the present invention is used for the organelle specific photo-activatable fluorescence imaging and has very good effects.

Another object of the present invention is to provide a method for preparing the above-mentioned photo-activatable aggregation-induced emission probe with in-situ generation capability.

A further object of the present invention is to provide an application of the above-mentioned photo-activatable aggregation-induced emission probe with in-situ generation capability. The photo-activatable aggregation-induced emission probe with in-situ generation capability can be used for biological imaging, especially for organelle specific fluorescence imaging.

The objects of the present invention are achieved by the following technical solution:

A photo-activatable aggregation-induced emission probe with in-situ generation capability is provided, having a structure as shown in the following formula III:

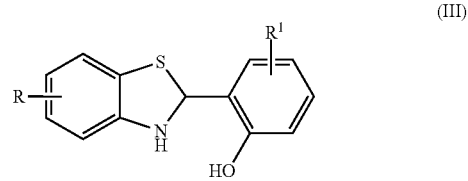

(III)

In formula III, R and $R^1$ are independently hydrogen, halogen, ester group, cyano group, nitro group, substituted or unsubstituted alkyl, alkoxy (R'—O—, R' alkyl), alkylamino group (R'—NH—, R'alkyl), alkylthio group (R'—S—, R'alkyl), aryl, heteroaryl, aryloxy (Ar—O—), arylamino group (Ar—NH—), arylthio group (Ar—S—), heteroaryloxy, heteroarylamino group, and heteroarylthio group;

the alkyl is a linear or branched alkyl; the substituted alkyl means that the hydrogen in the alkyl is replaced by a group formed by a cyclic compound, wherein the cyclic compound is preferably a cyclic compound formed by carbon and hydrogen and one or more of heteroatoms N, S and O, and more preferably morpholine;

the alkyl is a $C_{1-30}$ alkyl, the alkoxy is a $C_{1-30}$ alkoxy, the alkylamino group is a $C_{1-30}$ alkylamino group, and the alkylthio group is a $C_{1-30}$ alkylthio group;

the aryl refers to a monocyclic or polycyclic aromatic group with 6-20 carbon atoms, and the representative aryls include phenyl, naphthyl, anthracyl, and pyrenyl; the aryls in the aryloxy, arylamino group and arylthio group are each independently a monocyclic or polycyclic aromatic group with 6-20 carbon atoms, and the representative aryls include phenyl, naphthyl, anthracyl, and pyrenyl;

the heteroaryl refers to a monocyclic or polycyclic heteroaromatic group with 1-20 carbon atoms and 1-4 heteroatoms selected from N, S and O, and the representative heteroaryls include pyrrolyl, pyridyl, pyrimidinyl, imidazolyl, thiazolyl, indolyl, azanaphthyl, azaanthracyl, and azapyrenyl; the heteroaryls in the heteroaryloxy, heteroarylamino group, and heteroarylthio group are each independently a monocyclic or polycyclic heteroaromatic group with 1-20 carbon atoms and 1-4 heteroatoms selected from N, S and O, and the representative heteroaryls include pyrrolyl, pyridyl, pyrimidinyl, imidazolyl, thiazolyl, indolyl, azanaphthyl, azaanthracyl, and azapyrenyl.

Preferably, when R is hydrogen, $R^1$ is neither hydrogen nor methoxy.

A method for preparing a photo-activatable aggregation-induced emission probe with in-situ generation capability comprises the following steps: The photo-activatable aggregation-induced emission probe is obtained by reacting the compound of formula I with the compound of formula II;

the structure of the photo-activatable aggregation-induced emission probe is as shown in formula III:

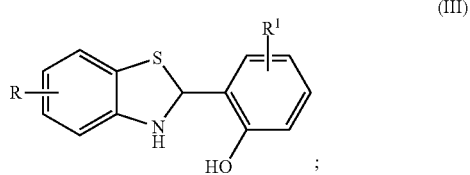

(III)

the compound of formula I is a bis(2-(2-hydroxybenzylidene)amino)aryl disulfide compound, having a structure as shown in the following formula 1:

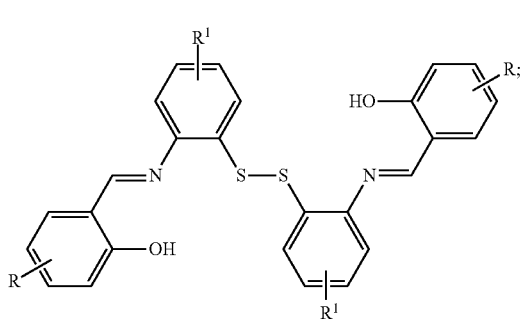

(I)

the compound of formula 11 is thiol, having a structure as shown in formula II:

HS—$R^2$    (II).

In formulas I and III, R and $R^1$ are independently hydrogen, halogen, ester group, cyano group, nitro group, substituted or unsubstituted alkyl, alkoxy (R'—O—, R' alkyl), alkylamino group (R'—NH—, R'alkyl), alkylthio group (R'—S—, R'alkyl), aryl, heteroaryl, aryloxy (Ar—O—), arylamino group (Ar—NH—), arylthio group (Ar—S—), heteroaryloxy, heteroarylamino group, and heteroarylthio group;

the alkyl is a linear or branched alkyl; the substituted alkyl means that the hydrogen in the alkyl is replaced by a group formed by a cyclic compound, wherein the cyclic compound is preferably a cyclic compound formed by carbon and hydrogen and one or more of heteroatoms N, S and O, and more preferably morpholine;

the alkyl is a $C_{1-30}$ alkyl, the alkoxy is a $C_{1-30}$ alkoxy, the alkylamino group is a $C_{1-30}$ alkylamino group, and the alkylthio group is a $C_{1-30}$ alkylthio group;

the aryl refers to a monocyclic or polycyclic aromatic group with 6-20 carbon atoms, and the representative aryls include phenyl, naphthyl, anthracyl, and pyrenyl;

the aryls in the aryloxy, arylamino group and arylthio group are each independently a monocyclic or polycyclic aromatic group with 6-20 carbon atoms, and the representative aryls include phenyl, naphthyl, anthracyl, and pyrenyl;

the heteroaryl refers to a monocyclic or polycyclic heteroaromatic group with 1-20 carbon atoms and 1-4 heteroatoms selected from N, S and O, and the representative heteroaryls include pyrrolyl, pyridyl, pyrimidinyl, imidazolyl, thiazolyl, indolyl, azanaphthyl, azaanthracyl, and azapyrenyl;

the heteroaryls in the heteroaryloxy, heteroarylamino group, and heteroarylthio group are each independently a monocyclic or polycyclic heteroaromatic group with 1-20 carbon atoms and 1-4 heteroatoms selected from N, S and O, wherein carbon and heteroatoms can form cyclic groups, and the representative heteroaryls include pyrrolyl, pyridyl, pyrimidinyl, imidazolyl, thiazolyl, indolyl, azanaphthyl, azaanthracyl, and azapyrenyl;

$R^2$ is a substituted or unsubstituted alkyl and aryl; the substituted alkyl is a hydroxyl substituted, ester-group substituted or carboxyl substituted alkyl; the hydroxyl substituted alkyl is an alkyl on which hydrogen is replaced by a hydroxyl, preferably —$CH_2$—$R_3$—OH, where $R_3$ is an alkylene (linear chain or branched chain); the ester-group substituted alkyl is an alkyl on which carbon is replaced by an ester group, preferably —$R_4$—COO—$R_5$, where $R_4$ is an alkylene (linear chain or branched chain), and $R_5$ is an alkyl (linear chain or branched chain); the carboxyl substituted alkyl is an alkyl on which carbon is replaced by a carboxyl, preferably —$R_4$—COOH, where $R_4$ is an alkylene (linear chain or branched chain); the thiol may also be mercapto-containing amino acid or mercapto-containing polypeptide.

The alkyl is a linear or branched alkyl, preferably a $C_{1-30}$ alkyl.

In the above preparation method, the reaction is carried out in an organic solvent; the organic solvent is more than one of dimethyl sulfoxide, N,N-dimethylfomamide, acetone, acetonitrile, dichloromethane, trichloromethane or tetrahydrofuran;

the reaction temperature is 15° C. to 40° C., preferably room temperature, more preferably 20° C. to 30° C.; the reaction time is 1-30 min; and the molar ratio of the compound of formula I to the compound of formula II is from 1:2 to 1:10.

The compound of formula I is a bis(2-(2-hydroxybenzylidene)amino)aryl disulfide compound, which is prepared through the following steps:

(S1) Dissolving a compound of formula V in an organic solvent, and adding hydrogen peroxide at 20° C. to 60° C. to generate a compound of formula VI; and (S2) reacting the compound of formula VI with a compound of formula VII under reflux in an organic solvent to obtain the compound of formula I; in the compound of formula V

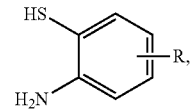

the compound of formula VI

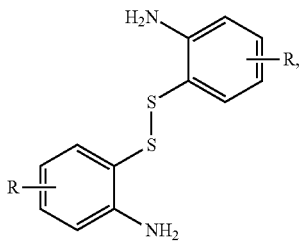

and the compound of formula VII

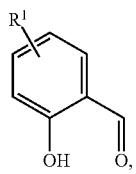

the definitions of the substituents R and $R^1$ are the same as in the compound of formula I.

The organic solvent in step S1 is more than one of methanol, ethanol, acetic acid, N,N-dimethylformamide, acetone, acetonitrile, dichloromethane, trichloromethane, tetrahydrofuran, and dimethyl sulfoxide; the reaction time is 1-30 min;

in step S1, the molar ratio of the compound of formula V to hydrogen peroxide is from 1:1 to 1:5, and the temperature is preferably 30° C. to 50° C.; in step S2, the reflux reaction temperature is 50° C. to 80° C., and the reflux reaction time is 10-60 min; the organic solvent in step S2 is more than one of methanol, ethanol, acetic acid, N,N-dimethylformamide, acetonitrile, dichloromethane, trichloromethane, tetrahydrofuran, and dimethyl sulfoxide;

in step S2, the catalyst is more than one of acetic acid, formic acid, hydrochloric acid, and sulfuric acid.

The compound of formula VI is a bis(2-amino)aryl disulfide compound; and the molar ratio of the compound of formula VI to the compound of formula VII is from 1:2 to 1:4.

The compound of formula I is a bis(2-(2-hydroxybenzylidene)amino)aryl disulfide compound, which is prepared through the following reaction equation:

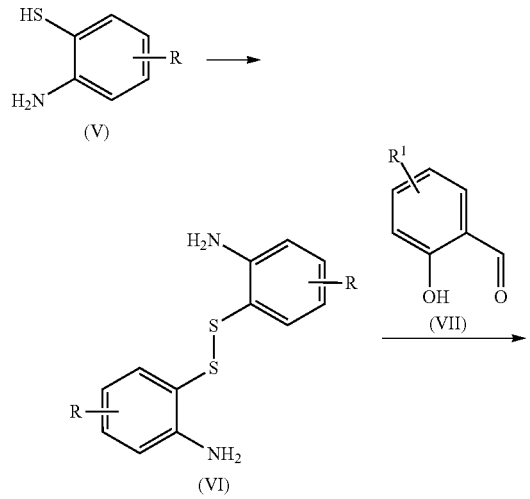

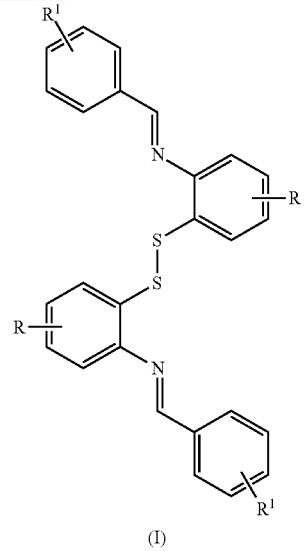

Another preparation method of the photo-activatable aggregation-induced emission probe with in-situ generation capability (formula III, a 2-(2-hydroxyphenyl)benzothiazoline compound) comprises the following steps: The compound of formula V is reacted with the compound of formula VII in the dark in an organic solvent and a protective gas to obtain the photo-activatable aggregation-induced emission probe. The compound of formula V and the compound of formula VII are the same as the compound of formula V and the compound of formula VII described above (in the preparation of the compound of formula I). The temperature of the reaction in the dark is 20° C. to 60° C., preferably 20° C. to 30° C.; the protective gas is nitrogen; the organic solvent is more than one of methanol, ethanol, acetonitrile, tetrahydrofuran, and N,N-dimethylformamide; and the molar ratio of the compound of formula V to the compound of formula VII is from 1:1 to 1:4.

The above 2-(2-hydroxyphenyl)benzothiazoline compound (formula III) is prepared through the following reaction equation:

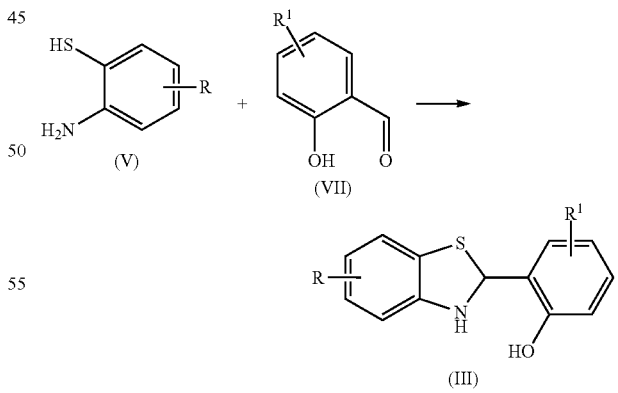

An aggregation-induced emission compound is a 2-(2-hydroxyphenyl)benzothiazole compound (formula IV), which is prepared through the following steps: The photo-activatable aggregation-induced emission probe (formula III) with in-situ generation capability is subjected to photo-oxidation to obtain an aggregation-induced emission compound.

The light used is ultraviolet light, the photo-oxidation refers to the use of ultraviolet light irradiation to photo-activate the aggregation-induced emission probe under an aerobic condition to undergo an oxidation reaction to generate an aggregation-induced emission compound.

It was found through study that the bis(2-(2-hydroxybenzylidene)amino)aryl disulfide compound (formula I) generated the 2-(2-hydroxyphenyl)benzothiazoline compound (formula III) in situ under the action of the thiol (formula II), and further underwent photo-oxidative dehydrogenation to produce the 2-(2-hydroxyphenyl)benzothiazole compound (formula IV), which exhibited the aggregation-induced emission property.

The reaction equation of this process is as follows:

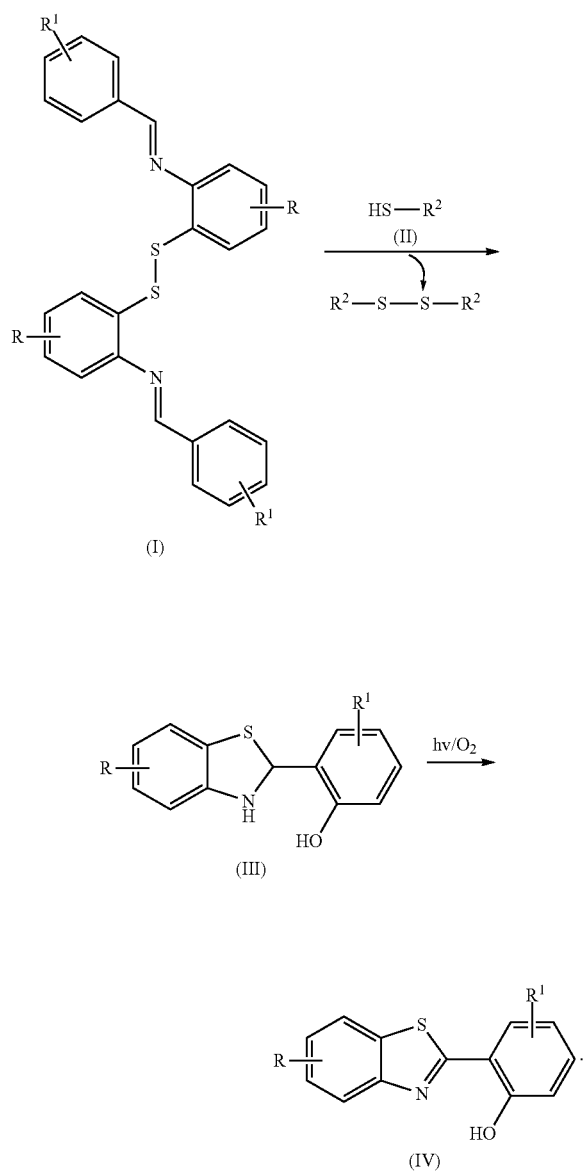

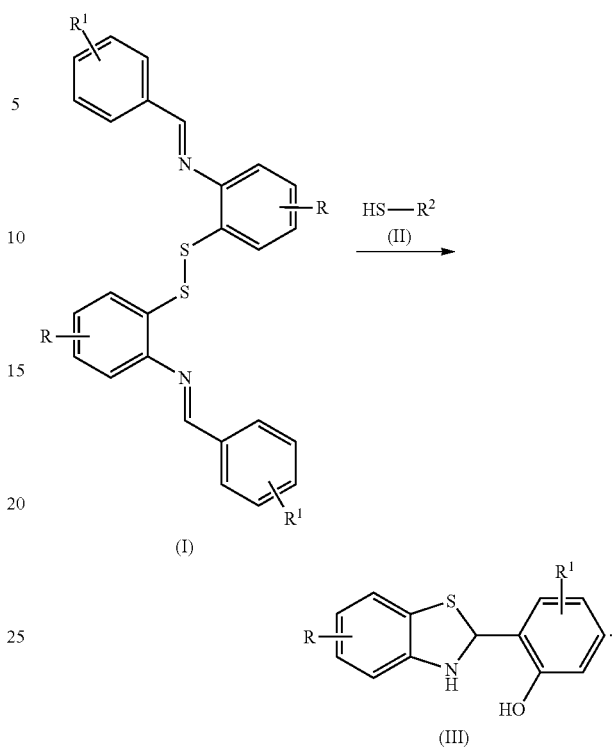

The compound of formula I and the compound of formula II (thiol) are used to generate the compound of formula III (the 2-(2-hydroxyphenyl)benzothiazoline compound) in situ through the following reaction equation:

The photo-activatable aggregation-induced emission probe with in-situ generation capability can be used for biological imaging, especially for organelle specific fluorescence imaging, achieving fluorescence imaging by photo-activation.

The above bis(2-(2-hydroxybenzylidene)amino)aryl disulfide compound (formula I) undergoes a reduction reaction with the thiol (formula II) to produce the 2-(2-hydroxyphenyl)benzothiazoline compound (formula III) in situ. Under ultraviolet light irradiation, the compound of formula III undergoes a photo-oxidative dehydrogenation reaction to produce the 2-(2-hydroxyphenyl)benzothiazole compound (formula IV) with the aggregation-induced emission property. By co-dyeing with commercial organelle dyes, the compound of formula IV is confirmed to have an excellent organelle specific dyeing effect, and can also selectively realize photo-activatable fluorescence imaging for a single cell or cell population in a multicellular environment.

It is worth noting that the 2-(2-hydroxyphenyl)benzothiazole compound produced by the photo-activatable aggregation-induced emission probe of the present invention with in-situ generation capability through the photo-oxidation reaction under the irradiation of ultraviolet light exhibits the aggregation-induced emission property. This means that the 2-(2-hydroxyphenyl)benzothiazoline compound can be used for photo-activatable fluorescence imaging even at high concentrations, and thus effectively overcome the defects of traditional fluorescent dyes, which undergo aggregation-induced quenching at high concentrations. In addition, the photo-activatable probe generated in situ, i.e. the 2-(2-hydroxyphenyl)benzothiazoline compound, does not itself have the property of fluorescence imaging or aggregation-induced emission; the reason why it exhibits the aggregation-induced emission property is that it will be converted under the irradiation of light into the 2-(2-hydroxyphenyl)benzothiazole compound, which has the aggregation-induced emission property.

In the present invention, "aggregation-induced emission" refers to a phenomenon in which a fluorescent compound hardly emits light in a dilute solution, but emits strong fluorescence in an aggregation state or solid state. For example, in the present invention, due to restriction of intramolecular motion and twisted intramolecular charge transfer mechanism, the 2-(2-hydroxyphenyl)benzothiazole compound does not emit fluorescence in the solution state or emits very weak light, but emits strong fluorescence in the aggregation state. In the present invention, "photo-activatable fluorescent probe" refers to a molecule with fluorescence emission capability generated by a kind of light-responsive molecule that undergoes a chemical reaction under the irradiation of light, and has such advantages as easy regulation and high spatiotemporal resolution in biological imaging.

The present invention has the following advantages and effects relative to the prior art:

(1) The photo-activatable aggregation-induced emission probe with in-situ generation capability of the present invention has the advantages of high in-situ generation efficiency, high photo-activation efficiency, high signal-to-noise ratio, low cytotoxicity, large Stokes shift, strong ability to enter cells, easy storage and use, and the like;

(2) photo-activatable aggregation-induced emission probe with in-situ generation capability of the present invention is generated by in-situ reaction without the necessity of separation, and can be directly used for organelle-targeted specific photo-activatable fluorescence imaging in living cells; and (3) the aggregation-induced emission compound of the present invention has the advantages of aggregation-induced emission, and can effectively overcome the defects of aggregation-induced quenching of traditional fluorescent dyes.

DETAILED DESCRIPTION OF THE EMBODIMENTS

Figure 1:
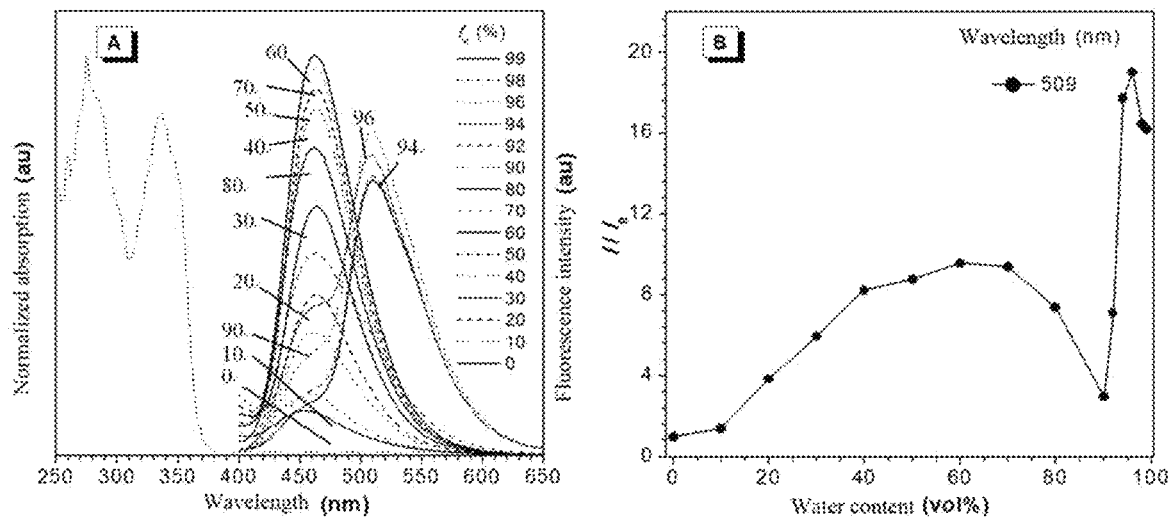
FIG. 1 shows the ultraviolet absorption and fluorescence emission spectra of compound IV-1: (A) the normalized ultraviolet absorption spectrum of compound IV-1 in tetrahydrofuran (left), and the fluorescence emission spectrum of compound IV-1 in the mixed solution of tetrahydrofuran and water with the increasing water content ($10^{-5}$ mol/L, right); and (B) the fluorescence intensity ratio change of compound IV-1 at 509 nm in the mixed solution of tetrahydrofuran and water.

The present invention will be further described in detail below with reference to examples and drawings, but the embodiments of the present invention are not limited thereto.

Example 1: Synthesis of compounds I-1 to I-3

Compound I-1: (2,2'-((1E,1'E)-((dithiobis(2,1-phenylene))di(imino))di(methylene)) diphenol)

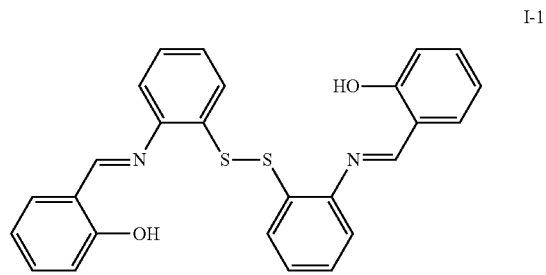 [SMILES: Oc1ccccc1/C=N/c1ccccc1SSc1ccccc1/N=C/c1ccccc1O]

I-1

First dissolving 2,2'-disulfide diphenylamine (248 mg, 1 mmol) in ethanol (10 mL), then adding 2-hydroxybenzaldehyde (305 mg, 2.5 mmol) to the solution, and then adding a drop of acetic acid as a catalyst, so as to allow a reflux reaction for 1 h; after the reaction, restoring the reaction solution to room temperature and then filtering the solution, washing the resulting filter residue with ethanol, and then drying the residue in vacuum to obtain a yellow solid product (433 mg, yield 95%). The relevant structural characterization data are as follows: $^1$H NMR (DMSO-d$_6$, 500 MHz): δ 12.57 (s, 2H), 9.03 (s, 2H), 7.73 (q, J=1.5 Hz, 2H), 7.59 (dd, J$_1$=1.0 Hz, J$_2$=1.5 Hz, 2H), 7.52-7.49 (m, 4H), 7.39-7.29 (m, 4H), 7.04-7.00 (m, 4H); $^{13}$C NMR (d$_6$-DMSO, 125 MHz): 163.6, 160.1, 146.0, 133.9, 132.7, 130.3, 128.1, 127.9, 126.1, 119.4, 118.5, 116.7. HRMS (MALDI-TOF): m/z [M+H]$^+$ caled. for $C_{26}H_{21}N_2O_2S_2^+$, 457.1039, found, 457.1035.

Compound 1-2: (2,2'-((1E,1'E)-((dithiobis(2,1-phenylene))di(imino))di(methylene))di(4-methoxyphenol))

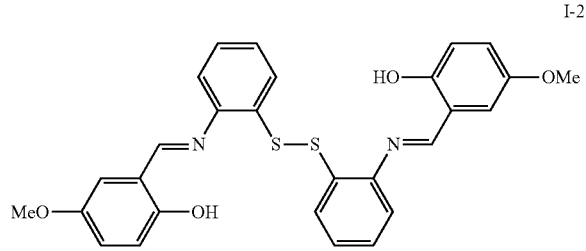 [SMILES: COc1ccc(O)c(/C=N/c2ccccc2SSc2ccccc2/N=C/c2cc(OC)ccc2O)c1]

I-2

Dissolving 2,2'-disulfide diphenylamine (248 mg, 1 mmol) in ethanol (5 mL), then adding the resulting solution dropwise to an ethanol (10 mL) solution of 5-methoxy-2-hydroxybenzaldehyde (380 mg, 2.5 mmol); after the dropwise addition, adding a drop of acetic acid to the reaction solution, and then allowing a reflux reaction under the protection of nitrogen for 1 h; after the reaction, restoring the reaction solution to room temperature and then filtering the solution, and then washing the filter residue with ethanol (10 mL×3) to obtain a yellow solid product (495 mg, yield 96%). The relevant structural characterization data are as follows: $^1$H NMR (d$_6$-DMSO, 500 MHz): 11.98 (s, 2H), 9.00 (s, 2H), 7.58 (dd, J$_1$=1 Hz, J$_2$=1.5 Hz, 2H), 7.48 (q, J=1 Hz, 2H), 7.37(td, J$_1$=7.5 Hz, J$_2$=1.5 Hz, 2H), 7.32-7.30 (m, 4H), 7.10 (q, 3 Hz, 2H), 3.77 (s, 6H); $^{13}$C NMR (d$_6$-DMSO, 125 MHz): 163.0, 154.3 151.2, 146.1, 130.4, 128.1, 127.9, 126.0, 121.2, 119.3, 118.3, 117.0, 115.1, 55.6. HRMS (MALDI-TOF): nm/z [M+H]$^+$ calcd. for C$_{28}$H$_{25}$N$_2$O$_4$S$_2$$^+$, 517.1250, found, 517.1301.

Compound 1-3: (2,2'-((1E,1'E)-((dithiobis(2,1-phenylene))di(imino))di(methylene)) di(4-morpholinomethyl)phenol))

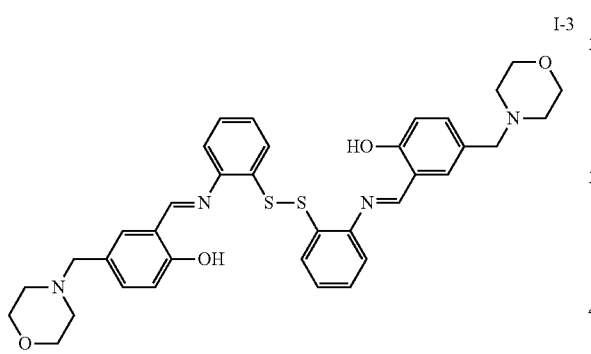

I-3

Dissolving 2,2'-disulfide diphenylamine (62 mg, 0.3 mmol) in ethanol (5 mL), then adding the resulting solution dropwise to an ethanol (5 mL) solution of 5-morpholinomethyl-2-hydroxybenzaldehyde (130 mg, 0.6 mmol); after the dropwise addition, adding a drop of acetic acid as a catalyst to the reaction solution, and then allowing a reflux reaction under the protection of nitrogen for 1 h; after the reaction, restoring the reaction solution to room temperature and then filtering the solution, and then washing the filter residue with ethanol (10 mL×3) to obtain a light-yellow solid product (152 mg, yield 78%). The relevant structural characterization data are as follows: $^1$H NMR (DMSO-d$_6$, 500 MHz): δ 12.51 (s, 2H), 9.03 (s, 2H), 7.65 (d, J=1.5 Hz, 2H), 7.58 (J$_1$=7.5 Hz, J$_2$=1.5 Hz, 2H), 7.51(dd, J$_1$=7.5 Hz, J$_2$=1.0 Hz, 2H), 7.41-7.35 (m, 4H), 7.31-7.28 (m, 4H), 6.97 (d, J=8.5 Hz, 2H), 3.58 (t, J=4.5 Hz, 8H), 3.44 (s, 4H), 2.37 (s, 8H); $^{13}$C NMR (DMSO-d$_6$, 125 MHz): 163.6, 159.2, 146.1, 134.7, 132.9, 130.3, 128.6, 128.2, 127.9, 126.1, 119.0, 118.5, 116.6, 66.2, 61.6, 53.1. HRMS (ESI): m/z [M+H]$^+$ calcd. for C$_{36}$H$_{39}$N$_4$O$_4$S$_2$$^+$, 655.2407, found, 655.2415.

Example 2: Synthesis of compounds III-1 to III-3

(1) Synthesis of compound III-1: 2-(2,3-dihydrobenzo[d]thiazol-2-yl)phenol

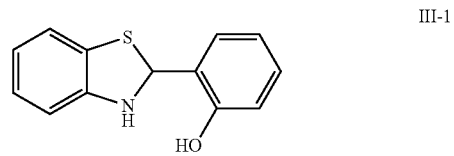 [SMILES: Oc1ccccc1C1Nc2ccccc2S1]

III-1

Method 1: Dissolving 2-aminothiophenol (625 mg, 5 mmol) and 2-hydroxybenzaldehyde (610 mg, 5 mmol) in methanol (5 mL), and then reacting in the dark at room temperature under the protection of nitrogen for 20 min; after the reaction, filtering the reaction solution, washing the resulting filter residue with methanol, and then drying the residue in vacuum to obtain a white solid product (960 mg, yield 84%) (method 1-compound III-1). $^1$H NMR (DMSO-d$_6$, 500 MHz): δ 9.81 (s, 1H), 7.38 (d, J=8.0 Hz, 1H), 7.10 (td, J$_1$=7.5 Hz, J$_2$=1.0 Hz, 1H), 6.94 (d, J=7.5 Hz, 1H) 6.88-6.76 (m, 4H), 6.66 (d, J=8.0 Hz, 1H), 6.56 (t, J=7.5 Hz, 1H), 6.47 (s, 1H); $^{13}$C NMR (DMSO-d$_6$, 125 MHz): 153.5, 147.8, 129.6, 128.6, 125.9, 125.2, 125.1, 121.2, 118.8, 118.5, 114.9, 108.6, 63.0.

Method 2: Mixing compound 1-1 (10.0 mM, 100 μL) with a dimethyl sulfoxide solution of ethyl mercaptoacetate (20.0 mM, 100 μL), and reacting at room temperature to get all transformed within 10 min, i.e., in-situ generating compound III-1 (in-situ compound III-1).

(2) Synthesis of compound III-2: 2-(2,3-dihydrobenzo[d]thiazol-2-yl)-4-methoxyphenol

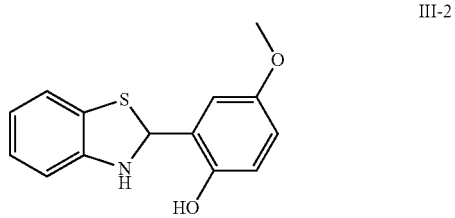 [SMILES: COc1ccc(O)c(C2Nc3ccccc3S2)c1]

III-2

Method 1: Dissolving 2-aminothiophenol (625 mg, 5 mmol) and 2-hydroxy-5-methoxybenzaldehyde (760 mg, 5 mmol) in methanol (10 mL), and then reacting in the dark at room temperature under the protection of nitrogen for 20 min; after the reaction, filtering the reaction solution, washing the resulting filter residue with methanol, and then drying the residue in vacuum to obtain a white solid product (776 mg, yield 60%) (method 1-compound III-2). $^1$H NMR (DMSO-d$_6$, 500 MHz): δ 9.35 (s, 1H), 6.95-6.93 (m, 2H), 6.86 (td, J$_1$=9.5 Hz, 12=1.5 Hz, 1H), 6.78-6.65 (m, 4H), 6.57 (td, J$_1$=9.5 Hz, J$_2$=1.5 Hz, 1H), 6.43 (d, J=3.0 Hz, 1H), 3.62 (s, 3H); $^{13}$C NMR (DMSO-d$_6$, 125 MHz): 152.0, 147.7, 147.3, 130.3, 125.2, 125.1, 121.2, 118.6, 115.5, 113.2, 111.9, 108.7, 63.2, 55.3.

Method 2: Mixing compound I-2 (10.0 mM, 100 μL) with a dimethyl sulfoxide solution of ethyl mercaptoacetate (20.0 mM, 100 μL), and reacting at room temperature to get all transformed within 10 min, i.e., in-situ generating compound III-2 (in-situ compound III-2).

(3) Synthesis of compound III-3: 2-(2,3-dihydrobenzo[d]thiazol-2-yl)-4-(morpholinomethyl)phenol

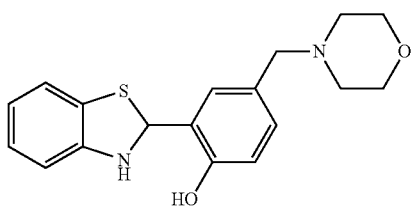

III-3

Method 1: Dissolving 2-aminothiophenol (125 mg, 1 mmol) and 2-hydroxy-5-(morpholinomethyl)benzaldehyde (221 mg, 5 mmol) in methanol (5 mL), and then reacting at room temperature under the protection of nitrogen for 20 min; after the reaction, spinning the reaction solution dry, then adding 2 mL of methanol to recrystallize, filtering, and drying the filter residue in vacuum to obtain a white solid product (171 mg, yield 52%) (method 1-compound III-3). $^1$H NMR (DMSO-d$_6$, 500 MHz): δ 9.75 (s, 11H), 7.37 (d, J$_1$=2.0 Hz, 1H), 7.02 (dd, J$_2$ 8.5 Hz, 12=2.0 Hz, 11H), 6.93 (d, J=7.5 Hz, 11H), 6.86 (td, J$_1$=7.5 Hz, J$_2$=1.0 Hz, 11H), 6.76 (d, J=8.0 Hz, 2H), 6.65 (d, J=7.5 Hz, 1H), 6.56 (td, J$_1$=7.5 Hz, J$_2$=1.0 Hz, 11H), 6.50 (d, J=2.5 Hz, 11H), 3.51 (t, J=4.5 Hz, 4H), 3.30 (d, J=5.0 Hz, 2H), 2.27 (s, 4H); $^{13}$C NMR (DMSO-d$_6$, 125 MHz): 152.7, 147.8, 129.3, 128.9, 127.7, 126.7, 125.3, 125.1, 121.1, 118.4, 114.6, 108.6, 66.1, 63.3, 62.2, 53.0.

Method 2: Mixing compound 1-3 (10.0 mM, 100 μL) with a dimethyl sulfoxide solution of ethyl mercaptoacetate (20.0 mM, 100 μL), and reacting at room temperature to get all transformed within 10 min, i.e., in-situ generating compound III-3 (in-situ compound III-3).

Example 3: Synthesis of compounds IV-1 to IV-3

Synthesis of compound IV-1:
2-(benzo[d]thiazol-2-yl)phenol

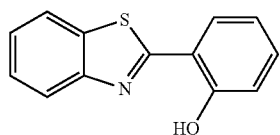

IV-1

Method 1: Subjecting the in-situ generated compound III-1 (i.e., in-situ compound III-1) to a photo-oxidation reaction under the irradiation of ultraviolet light for 10 h to obtain compound IV-1 (in-situ compound IV-1).

Method 2: Dissolving 2-aminothiophenol (250 mg, 2 mmol) and 2-hydroxybenzaldehyde (244 mg, 2 mmol) in methanol (5 mL), then adding dropwise to the resulting solution concentrated hydrochloric acid (37%, 169 μL) and hydrogen peroxide (30% aq, 188 μL), and then reacting in air at room temperature for 2 h; after the reaction, filtering the reaction solution, washing the resulting filter residue with methanol, and then drying the residue in vacuum to obtain a white solid product (435 mg, yield 96%) (i.e., method 2-compound IV-1). The relevant structural characterization data are as follows: $^1$H NMR (DMSO-d$_6$, 500 MHz): δ 11.59 (s, 1H), 8.19-8.06 (m, 3H), 7.57-7.40 (m, 3H), 7.10-7.01 (in, 2H); $^{13}$C NMR (DMSO-d$_6$, 125 MHz): 165.2, 156.2, 151.4, 134.2, 132.5, 128.5, 126.5, 125.1, 122.1, 122.0, 119.8, 118.3, 116.9. HRMS (ESI): m/z [M+H]$^+$ calcd. for C$_{13}$H$_{10}$NOS$^+$, 228.0478, found, 228.0475.

Synthesis of compound IV-2:
2-(benzo[d]thiazol-2-yl)-4-methoxyphenol

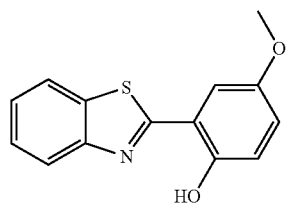

IV-2

Method 1: Subjecting the in-situ generated compound III-2 (i.e., in-situ compound III-2) to a photo-oxidation reaction under the irradiation of ultraviolet light for 10 h to obtain compound IV-2 (in-situ compound IV-2).

Method 2: Dissolving 2-aminothiophenol (250 mg, 2 mmol) and 2-hydroxy-5-methoxybenzaldehyde (304 mg, 2 mmol) in methanol (5 mL), then adding dropwise to the resulting solution concentrated hydrochloric acid (37%, 169 μL) and hydrogen peroxide (30% aq, 188 μL), and then reacting in air at room temperature for 2 h; after the reaction, filtering the reaction solution, washing the resulting filter residue with methanol, and then drying the residue in vacuum to obtain a light-yellow solid product (493 mg, yield 96%) (i.e., method 2-compound IV-2). The relevant structural characterization data are as follows: $^1$H NMR (DMSO-d$_6$, 500 MHz): δ 11.03 (s, 1H), 8.14 (d, J=8.0 Hz, 1H), 8.07 (d, J=8.0 Hz, 1H), 7.72 (d, J=3.0 Hz, 1H), 7.54 (td, J$_1$=8.0 Hz, J$_2$=1.0 Hz, 1H), 7.44 (td, J=8.0 Hz, J$_2$=1.0 Hz, 1H), 7.06-7.01 (m, 2H), 3.81 (s, 3H); $^{13}$C NMR (DMSO-d$_6$, 125 MHz): 163.7, 151.7, 150.8, 149.8, 134.2, 125.8, 124.4, 121.6, 121.4, 119.1, 118.1, 117.4, 110.5, 55.0. HRMS (ESI): m/z [M+H]$^+$ calcd. for C$_{14}$H$_{12}$NO$_2$S, 258.0583, found, 258.0581.

Synthesis of compound IV-3: 2-(benzo[d]thiazol-2-yl)-4-(morpholinomethyl)phenol

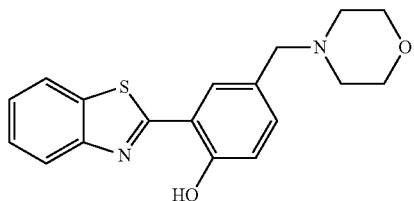

IV-3

Method 1: Subjecting the in-situ generated compound III-3 (i.e., in-situ compound III-3) to a photo-oxidation reaction under the irradiation of ultraviolet light for 10 h to obtain compound IV-3 (in-situ compound IV-3).

Method 2: Dissolving 2-aminothiophenol (63 mg, 0.5 mmol) and 2-hydroxy-5-morpholine methylbenzaldehyde (111 mg, 2 mmol) in methanol (5 mL), then adding dropwise to the resulting solution concentrated hydrochloric acid (37%, 42 μL) and hydrogen peroxide (30% aq, 47 μL), and then reacting in air at room temperature for 2 h; after the reaction, spinning the reaction solution dry, adding tetrahydrofuran to wash, and then drying the solid components in vacuum to obtain a gray solid product (124 mg, yield 76%) (i.e., method 2-compound IV-3). The relevant structural characterization data are as follows: $^1$H NMR (DMSO-d$_6$, 500 MHz): δ 12.04 (br s, 1H), 8.12 (d, J=8.0 Hz, 2H), 8.04 (d, J=8.0 Hz, 1H), 7.52 (t, J=7.5 Hz, 1H), 7.42 (t, J=7.5 Hz, 1H), 7.30 (d, J=8.0 Hz, 1H), 7.03 (d, J=8.5 Hz, 1H), 3.58 (s, 4H), 3.45 (s, 2H), 2.38 (s, 4H); $^{13}$C NMR (DMSO-d$_6$, 125 MHz): 165.1, 151.6, 135.1, 133.1, 128.5, 125.8, 124.2, 123.9, 121.7, 121.4, 118.5, 117.8,66.2,62.3,53.1. HRMS (ESI): n/z [M+H]$^+$ caled. for $C_1H_{19}N_2O_2S$, 327.1162, found, 327.1157.

Example 4

Characterization of Photophysical Properties of Compound IV-1:

Mixing tetrahydrofuran and water according to different volume ratios (tetrahydrofuran:water=100:0, 90:10, 80:20, 70:30, 60:40, 50:50, 40:60, 30:70, 20:80, 10:90, 8:92, 6:94, 4:96, 2:98, 1:99) to form mixed solutions with different water contents; dissolving compound IV-1 (i.e., method 2-compound IV-1) into these mixed solutions to make the concentration of the compound at 10' mol/L, and then detecting the fluorescence emission spectrum, with the results as shown in FIG. 1. FIG. 1 shows the ultraviolet absorption and fluorescence emission spectra of compound IV-1 (compound IV-1 prepared by method 2): (A) the normalized ultraviolet absorption spectrum of compound IV-1 in tetrahydrofuran (left), and the fluorescence emission spectrum of compound IV-1 in the mixed solution of tetrahydrofuran and water with the increasing water content ($10^{-5}$ mol/L, right); and (B) the fluorescence intensity ratio change of compound IV-1 at 509 nm in the mixed solution of tetrahydrofuran and water. When the water content in the mixed solution system was continuously increased, the intensity of the ketoluminescence (509 nm) gradually increased first (tetrahydrofuran:water varied from 100:0 to 40:60), and then decreased (tetrahydrofuran:water varied from 40:60 to 10:90); when the water content continued to increase (tetrahydrofuran:water varied from 10:90 to 4:96), the ketoluminescence increased rapidly, which was due to the decrease in solubility leading to the formation of aggregates, the formation of hydrogen bonds in the molecules and the limitation of intramolecular movement, showing the aggregation-induced emission property; when the water content was further increased (tetrahydrofuran:water varied from 4:96 to 1:99), the fluorescence intensity decreased slightly, which might be due to the rapid decrease in solubility, resulting in disordered aggregates.

The in-situ generated compound IV-1 (in-situ compound IV-1) had the same photophysical properties as method 2-compound IV-1.

Example 5

Figure 2:
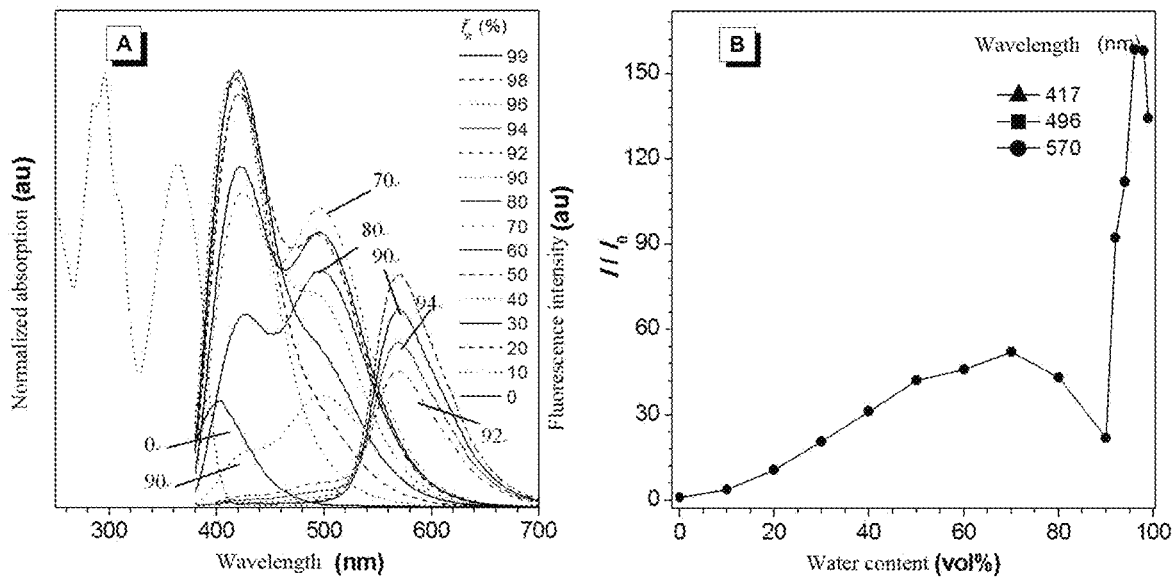
FIG. 2 shows the ultraviolet absorption and fluorescence emission spectra of compound IV-2: (A) the normalized ultraviolet absorption spectrum of compound IV-2 in tetrahydrofuran (left), and the fluorescence emission spectrum of compound IV-1 in the mixed solution of tetrahydrofuran and water with the increasing water content ($10^{-5}$ mol/L, right); and (B) the fluorescence intensity ratio change of compound IV-2 at 570 nm in the mixed solution of tetrahydrofuran and water.

Characterization of Photophysical Properties of Compound IV-2:

Mixing tetrahydrofuran and water according to different volume ratios (tetrahydrofuran:water=100:0, 90:10, 80:20, 70:30, 60:40, 50:50, 40:60, 30:70, 20:80, 10:90, 8:92, 6:94, 4:96, 2:98, 1:99) to form mixed solutions with different water contents; dissolving compound IV-2 (i.e., method 2-compound IV-2) into these mixed solutions to make the concentration of the compound at $10^0$ mol/L, and then detecting the fluorescence emission spectrum, with the results as shown in FIG. 2. FIG. 2 shows the ultraviolet absorption and fluorescence emission spectra of compound IV-2 (i.e., method 2-compound IV-2): (A) the normalized ultraviolet absorption spectrum of compound IV-2 in tetrahydrofuran (left), and the fluorescence emission spectrum of compound IV-1 in the mixed solution of tetrahydrofuran and water with the increasing water content ($10^{-5}$ mol/L, right); and (B) the fluorescence intensity ratio change of compound IV-2 at 570 nm in the mixed solution of tetrahydrofuran and water.

When the water content in the mixed solution system was continuously increased, the intensity of the ketoluminescence (570 nm) gradually increased first (tetrahydrofuran:water varied from 100:0 to 30:70), and then decreased (tetrahydrofuran:water varied from 30:70 to 10:90); when the water content continued to increase (tetrahydrofuran:water varied from 10:90 to 4:96), the ketoluminescence increased rapidly, which was due to the decrease in solubility leading to the formation of aggregates, the formation of hydrogen bonds in the molecules and the limitation of intramolecular movement, showing the aggregation-induced emission property; when the water content was further increased (tetrahydrofuran:water varied from 4:96 to 1:99), the fluorescence intensity decreased slightly, which might be due to the rapid decrease in solubility, resulting in disordered aggregates. The in-situ generated compound IV-2 (in-situ compound IV-2) had the same photophysical properties as method 2-compound IV-2.

Example 6

Figure 3:
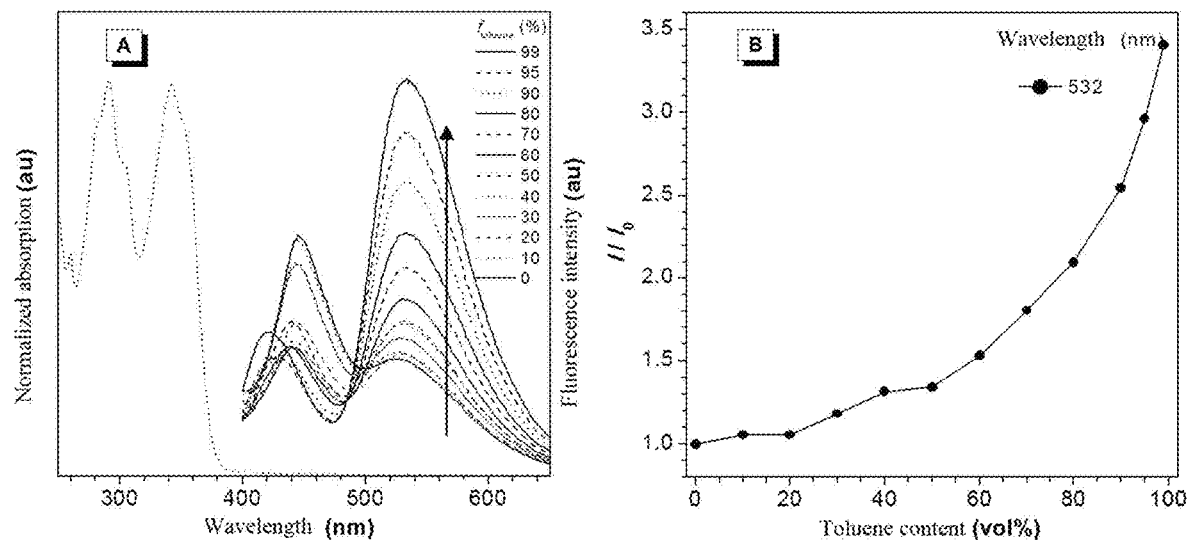
FIG. 3 shows the ultraviolet absorption and fluorescence emission spectra of compound IV-3: (A) the normalized ultraviolet absorption spectrum of compound IV-3 in tetrahydrofuran (left), and the fluorescence emission spectrum of compound IV-1 in the mixed solution of tetrahydrofuran and toluene with the increasing toluene content ($10^{-5}$ mol/L, right); and (B) the fluorescence intensity ratio change of compound IV-3 at 532 nm in the mixed solution of tetrahydrofuran and toluene.

Characterization of Photophysical Properties of Compound IV-3:

Mixing tetrahydrofuran and toluene according to different volume ratios (tetrahydrofuran:toluene=100:0, 90:10, 80:20, 70:30, 60:40, 50:50, 40:60, 30:70, 20:80, 10:90, 5:95, 1:99) to form mixed solutions with different toluene contents; dissolving compound IV-3 (i.e., method 2-compound IV-3) into these mixed solutions to make the concentration of the compound at 10 mol/L, and then detecting the fluorescence emission spectrum, with the results as shown in FIG. 3. FIG. 3 shows the ultraviolet absorption and fluorescence emission spectra of compound IV-3 (i.e., method 2-compound IV-3): (A) the normalized ultraviolet absorption spectrum of compound IV-3 in tetrahydrofuran (left), and the fluorescence emission spectrum of compound IV-1 in the mixed solution of tetrahydrofuran and toluene with the increasing toluene content ($10^{-5}$ mol/L, right); and (B) the fluorescence intensity ratio change of compound IV-3 at 532 nm in the mixed solution of tetrahydrofuran and toluene.

When the toluene content in the mixed solution system was continuously increased, the intensity of the ketoluminescence (532 nm) gradually increased, which was due to, with the increase of the toluene content, the decrease in solubility leading to the formation of aggregates, the formation of hydrogen bonds in the molecules and the limitation of intramolecular movement, showing the aggregation-induced emission property. The in-situ generated compound IV-3 (in-situ compound IV-3) had the same photophysical properties as method 2-compound IV-3.

Example 7

By measuring the quantum yield and fluorescence lifetime of compounds IV-1 (method 2-compound IV-1), IV-2 (method 2-compound IV-2) and IV-3 (method 2-compound IV-3) in tetrahydrofuran solution and solid state (thin film state)) (Table 1), the following results were found relative to the cases in the tetrahydrofuran solution: compound IV-1 in the thin film state increased by 94.4 times in the quantum yield, and increased by 6.0 times in the fluorescence lifetime; compound IV-2 in the thin film state increased by 33.4 times in the quantum yield, and increased by 5.2 times in the fluorescence lifetime; compound IV-3 in the thin film state increased by 25.8 times in the quantum yield, and increased by 4.1 times in the fluorescence lifetime; therefore, the aggregation-induced emission property of compound IV was confirmed. Moreover, the Stokes shift of compound IV in the thin film state was greater than 170 nm, which was far superior to the traditional fluorescent materials (having a Stokes shift usually less than 40 nm), very beneficial to its application in biological imaging. The in-situ compounds IV-1 to IV-3 also had the photophysical properties in Table 1.

TABLE 1

Photophysical properties of compounds IV-1, IV-2 and IV-3 in tetrahydrofuran solution and solid state

| | Tetrahydrofuran solution state ($10^{-5}$ mol/L) | | | | Solid state | | |
|---|---|---|---|---|---|---|---|
| IV | Absorption wavelength (nm) | Emission wavelength (nm) | Quantum yield (%) | Fluorescence lifetime (ns) | Emission wavelength (nm) | Quantum yield (%) | Fluorescence lifetime (ns) |
| IV-1 | 334 | 452 | 0.7 | 0.83 | 509 | 66.1 | 4.96 |
| IV-2 | 362 | 402 | 1.2 | 0.94 | 570 | 40.1 | 4.88 |
| IV-3 | 341 | 445 | 1.1 | 1.56 | 532 | 28.4 | 6.39 |

Example 8

Figure 4:
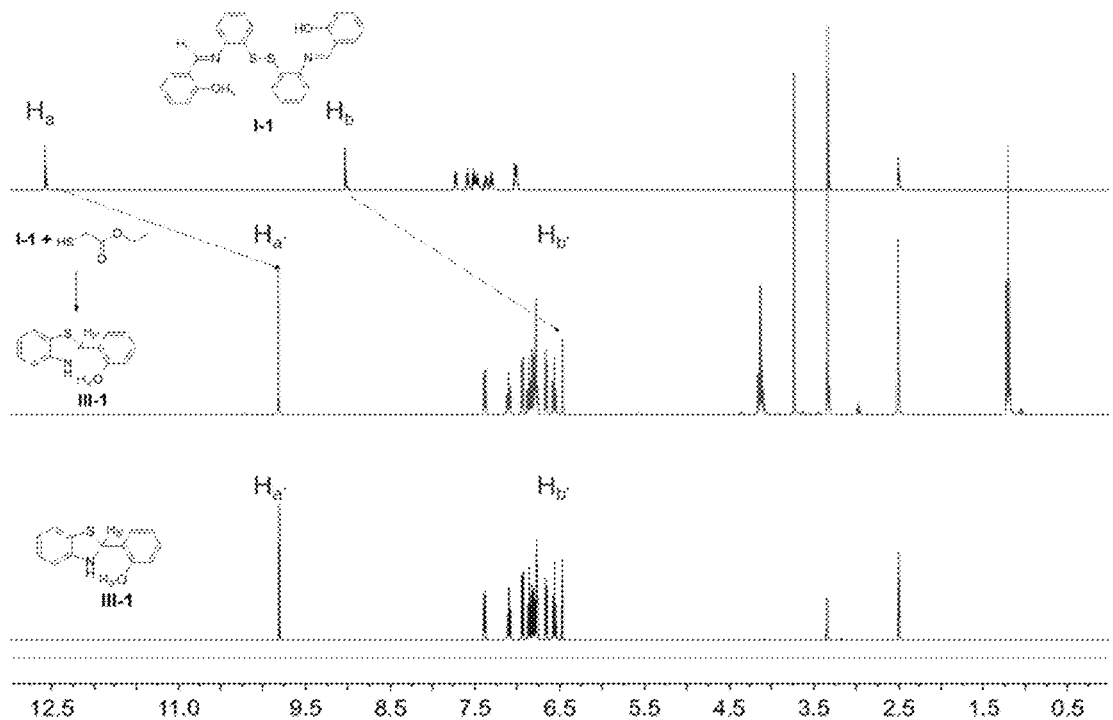
FIG. 4 shows the nuclear magnetic hydrogen spectrum overlay of compound I-1, compound III-1 (method 1-compound III-1) and the in-situ reaction product of compound 1-1 with ethyl mercaptoacetate.
Figure 5:
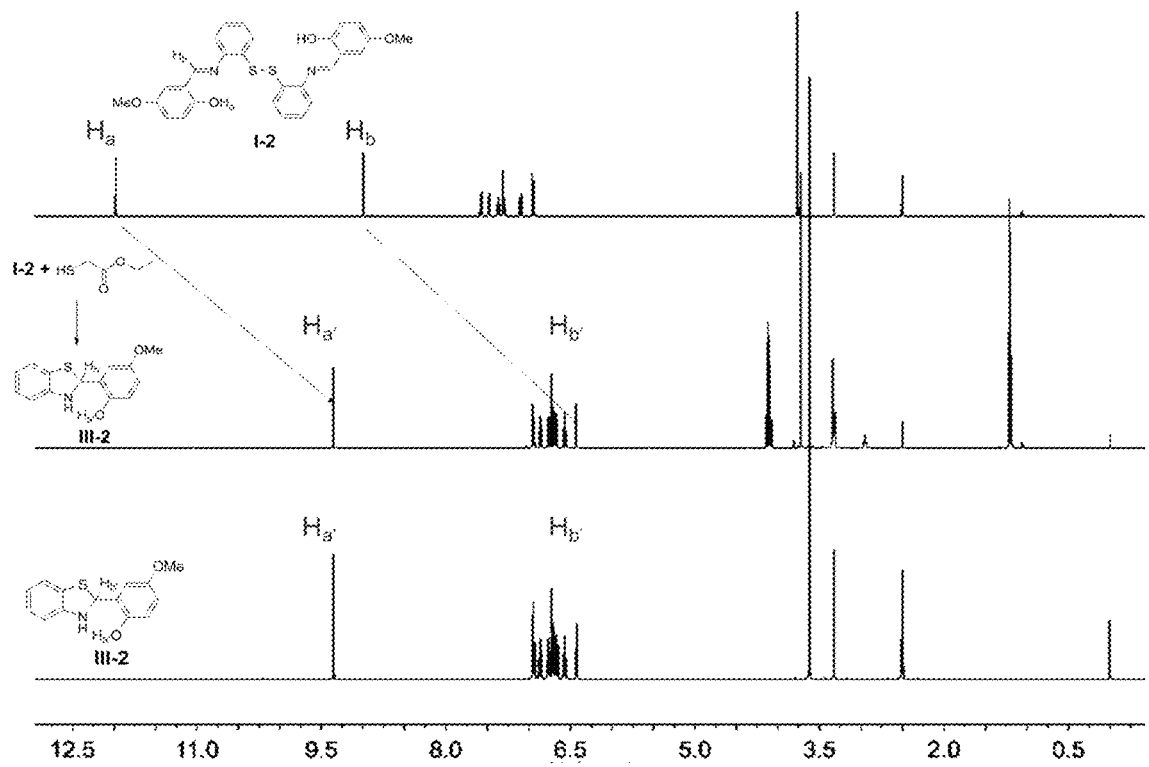
FIG. 5 shows the nuclear magnetic hydrogen spectrum overlay of compound 1-2, compound III-2 (method 1-compound III-2) and the in-situ reaction product of compound 1-2 with ethyl mercaptoacetate.
Figure 6:
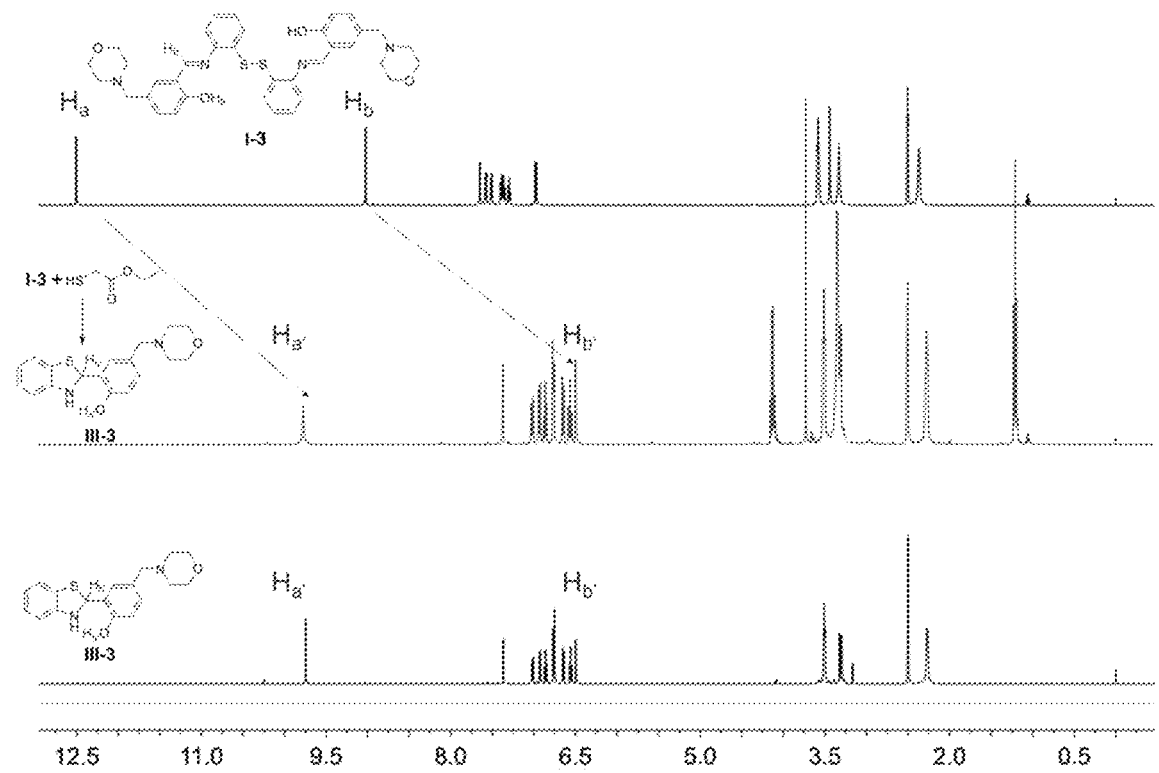
FIG. 6 shows the nuclear magnetic hydrogen spectrum overlay of compound I-3, compound III-3 (method 1-compound III-3) and the in-situ reaction product of compound 1-3 with ethyl mercaptoacetate.

Compounds 1-1 to I-3 in Example 1, method 1-compound III-1 to method 1-compound III-3 in Example 2, and the in-situ generated compounds III-1 to III-3 (in-situ compounds III-1 to III-3) were detected by nuclear magnetic hydrogen spectroscopy, with the test results as shown in FIGS. 4-6. Compounds 111-1 to III-3 generated in situ were converted into compounds IV-1 to IV-3 (in-situ compounds IV-1 to IV-3) by photo-oxidation under the irradiation of light, this conversion process being confirmed by nuclear magnetic hydrogen spectroscopy (see FIGS. 7-9).

FIG. 4 shows the nuclear magnetic hydrogen spectrum overlay of compound I-1, compound III-1 (method 1-compound III-1) and the in-situ reaction product of compound I-1 with ethyl mercaptoacetate (in-situ generated compound III-1); FIG. 5 shows the nuclear magnetic hydrogen spectrum overlay of compound I-2, compound III-2 (method 1-compound III-2) and the in-situ reaction product of compound 1-2 with ethyl mercaptoacetate (in-situ generated compound III-2); FIG. 6 shows the nuclear magnetic hydrogen spectrum overlay of compound I-3, compound III-3 (method 1-compound III-3) and the in-situ reaction product of compound 1-3 with ethyl mercaptoacetate (in-situ generated compound III-3).

Figure 7:
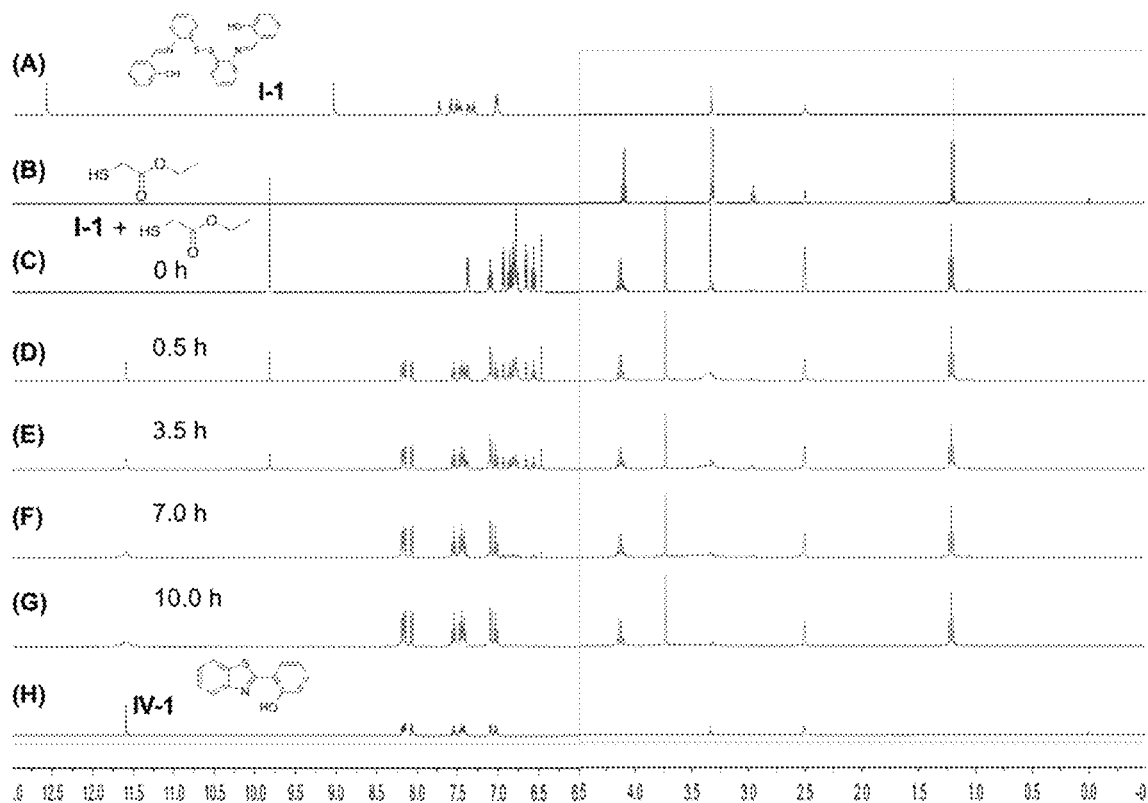
FIG. 7 shows the nuclear magnetic hydrogen spectrum overlay of compound I-1 and ethyl mercaptoacetate to produce compound III-1 through the in-situ reaction, and then produce compound IV-1 under the irradiation of ultraviolet light at 365 nm.
Figure 8:
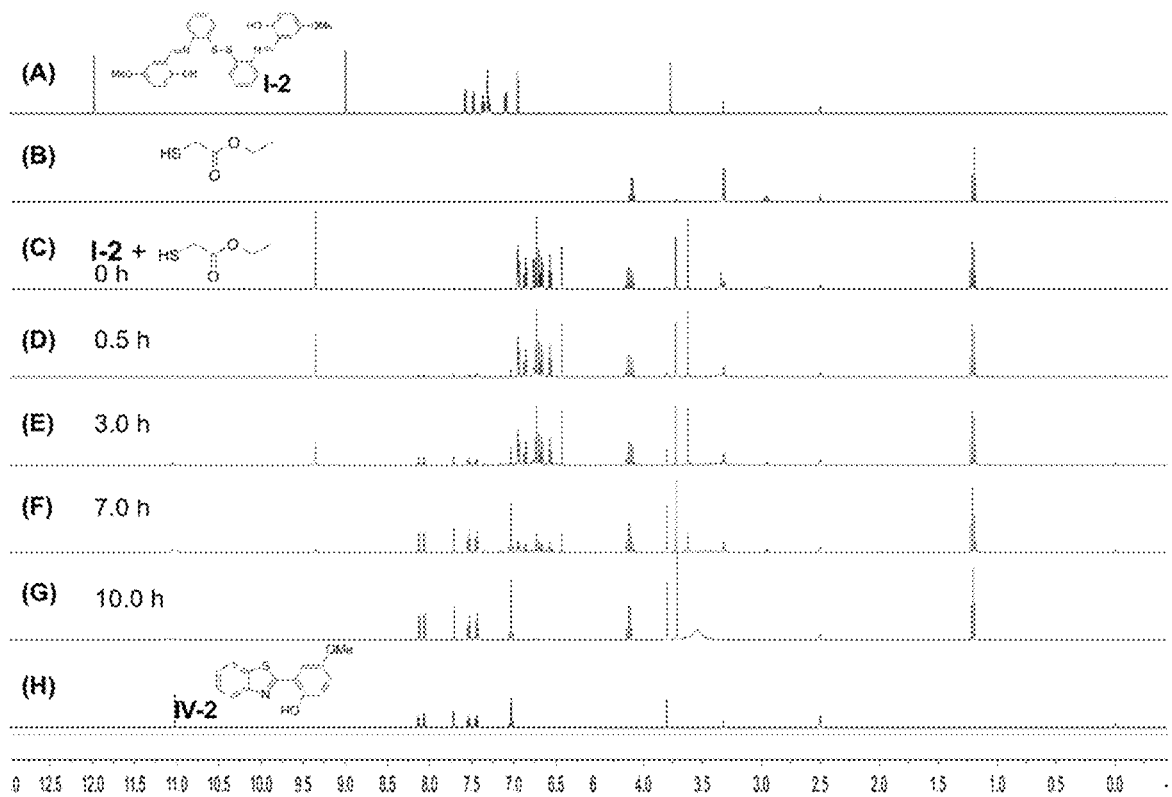
FIG. 8 shows the nuclear magnetic hydrogen spectrum overlay of compound I-2 and ethyl mercaptoacetate to produce compound III-2 through the in-situ reaction, and then produce compound IV-2 under the irradiation of ultraviolet light at 365 nm.
Figure 9:
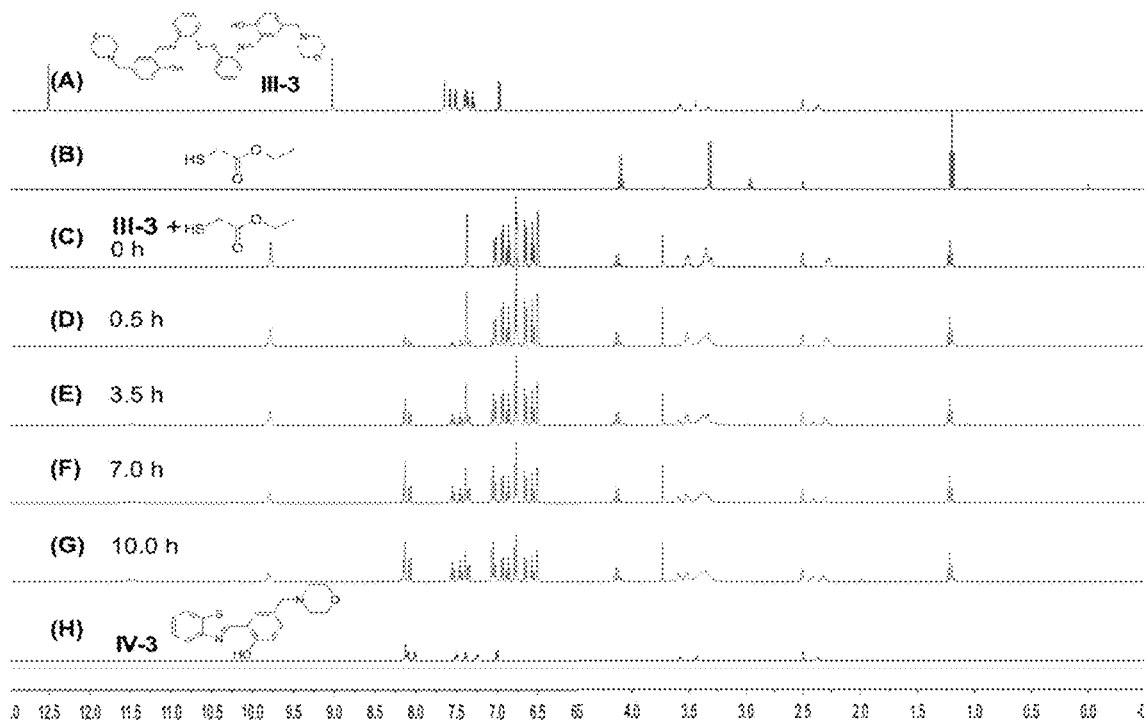
FIG. 9 shows the nuclear magnetic hydrogen spectrum overlay of compound I-3 and ethyl mercaptoacetate to produce compound III-3 through the in-situ reaction, and then produce compound IV-3 under the irradiation of ultraviolet light at 365 nm.

FIG. 7 shows the nuclear magnetic hydrogen spectrum overlay of compound I-1 and ethyl mercaptoacetate to produce compound III-1 (in-situ generated compound III-1) through the in-situ reaction, and then produce compound IV-1 under the irradiation of ultraviolet light at 365 nm; FIG. 8 shows the nuclear magnetic hydrogen spectrum overlay of compound I-2 and ethyl mercaptoacetate to produce compound III-2 through the in-situ reaction, and then produce compound IV-2 under the irradiation of ultraviolet light at 365 nm; FIG. 9 shows the nuclear magnetic hydrogen spectrum overlay of compound 1-3 and ethyl mercaptoacetate to produce compound III-3 through the in-situ reaction, and then produce compound IV-3 under the irradiation of ultraviolet light at 365 nm.

Example 9

In-situ generated compounds 11-1 to III-3 (in-situ compounds III-1 to III-3) could be converted into compounds IV-1 to IV-3 with the aggregation-induced emission property under the irradiation of light, this conversion process being confirmed by ultraviolet-visible absorption and fluorescence detection.

Figure 10:
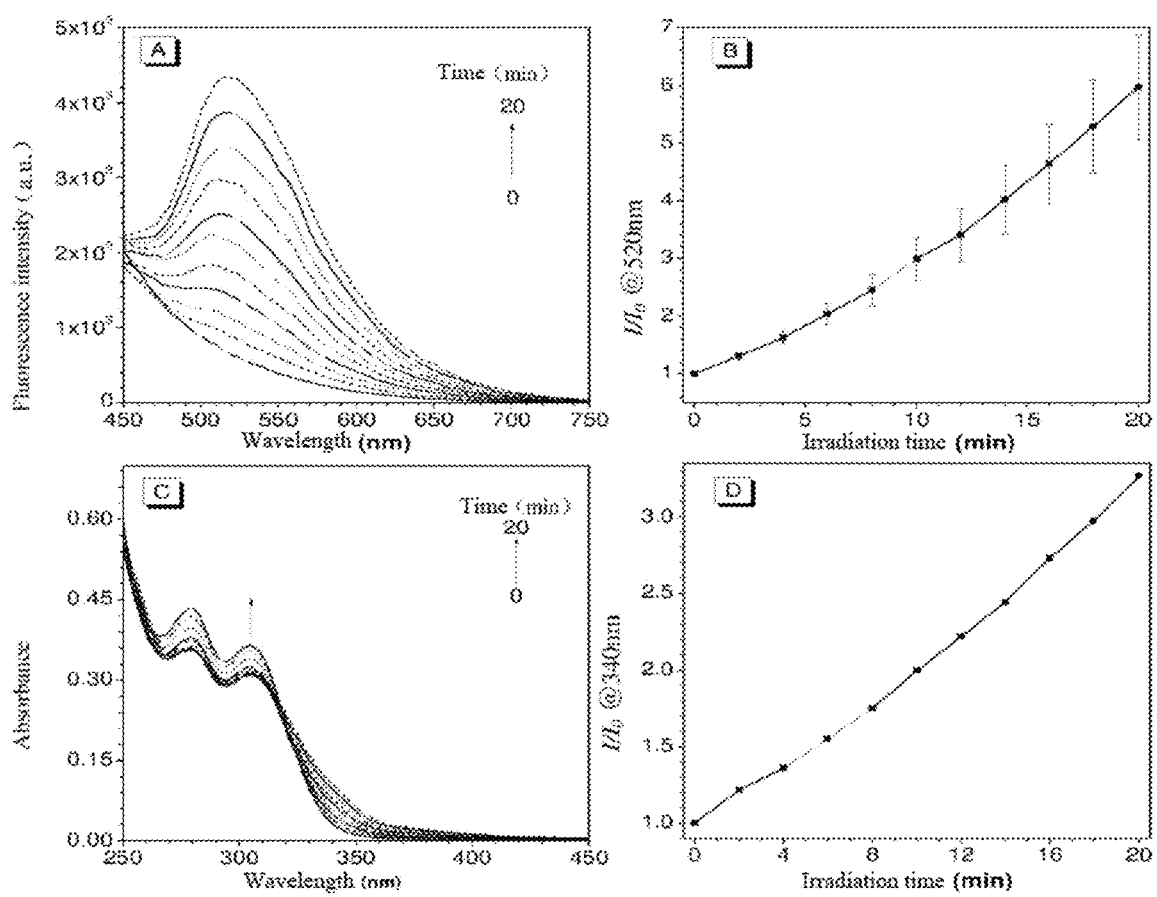
FIG. 10 shows (A) the fluorescence emission spectrum, (B) the fluorescence intensity ratio at 520 nm, (C) the ultraviolet-visible absorption spectrum, and (D) the absorption intensity ratio at 340 nm, of the in-situ generated compound III-1 in a mixed solution of dimethyl sulfoxide and water (in a volume ratio of dimethyl sulfoxide to water at 1:99, $10^{-4}$ mol/L) under the irradiation of 365 nm light with elapse of time.

In a water:dimethyl sulfoxide (99:1, v/v) solution under the irradiation of a 365 nm UV lamp, the in-situ generated compound III-1 gradually increased with the irradiation time both in the fluorescence intensity at 520 nm, and in the absorption intensity at 340 nm, which was due to compound IV-1 produced by photo-oxidative dehydrogenation of compound III-1 (see FIG. 10). The fluorescence and ultraviolet-visible absorption spectra of compounds III-2 to III-3 under the irradiation of a UV lamp also had similar changes (see FIGS. 11-12).

Figure 11:
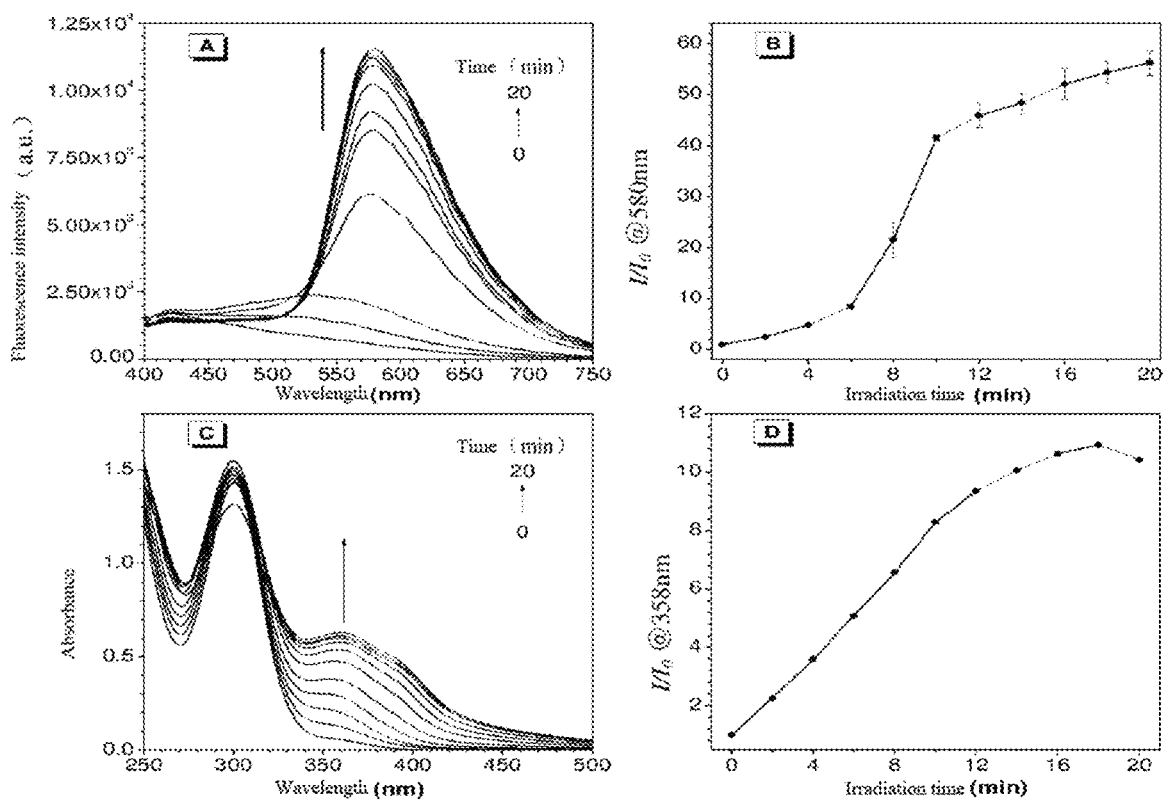
FIG. 11 shows (A) the fluorescence emission spectrum, (B) the fluorescence intensity ratio at 580 nm, (C) the ultraviolet-visible absorption spectrum, and (D) the absorption intensity ratio at 358 nm, of the in-situ generated compound III-2 in a mixed solution of dimethyl sulfoxide and water (in a volume ratio of dimethyl sulfoxide to water at 1:99, $10^{-4}$ mol/L) under the irradiation of 365 nm light with elapse of time.
Figure 12:
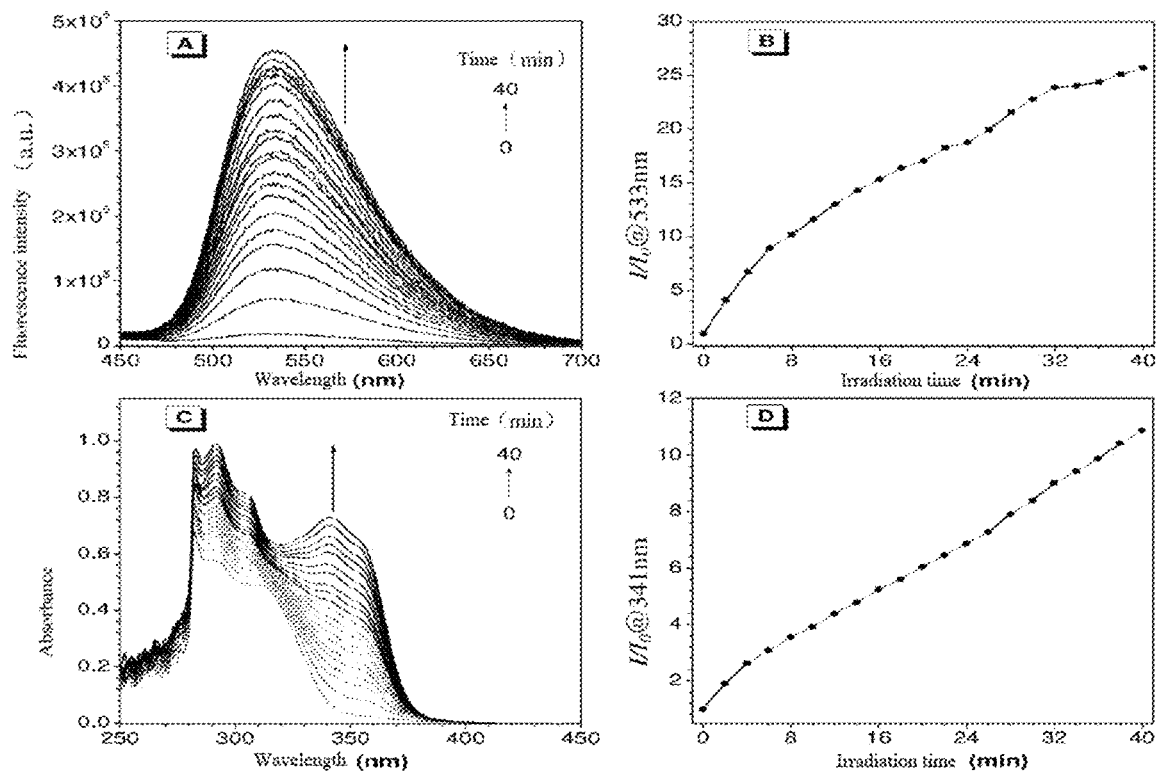
FIG. 12 shows (A) the fluorescence emission spectrum, (B) the fluorescence intensity ratio at 533 nm, (C) the ultraviolet-visible absorption spectrum, and (D) the absorption intensity ratio at 341 nm, of the in-situ generated compound III-3 in a mixed solution of dimethyl sulfoxide and water (in a volume ratio of dimethyl sulfoxide to water at 1:99, $10^{-4}$ mol/L) under the irradiation of 365 nm light with elapse of time.

FIG. 10 shows (A) the fluorescence emission spectrum, (B) the fluorescence intensity ratio at 520 nm, (C) the ultraviolet-visible absorption spectrum, and (D) the absorption intensity ratio at 340 nm, of the in-situ generated compound III-1 in a mixed solution of dimethyl sulfoxide and water (in a volume ratio of dimethyl sulfoxide to water at 1:99, 10V mol/L) under the irradiation of 365 nm light with elapse of time. FIG. 11 shows (A) the fluorescence emission spectrum, (B) the fluorescence intensity ratio at 580 nm, (C) the ultraviolet-visible absorption spectrum, and (D) the absorption intensity ratio at 358 nm, of the in-situ generated compound III-2 in a mixed solution of dimethyl sulfoxide and water (in a volume ratio of dimethyl sulfoxide to water at 1:99, $10^{-4}$ mol/L) under the irradiation of 365 nm light with elapse of time. FIG. 12 shows (A) the fluorescence emission spectrum, (B) the fluorescence intensity ratio at 533 nm, (C) the ultraviolet-visible absorption spectrum, and (D) the absorption intensity ratio at 341 nm, of the in-situ generated compound III-3 in a mixed solution of dimethyl sulfoxide and water (in a volume ratio of dimethyl sulfoxide to water at 1:99, 104 mol/L) under the irradiation of 365 nm light with elapse of time.

Example 10

Figure 13:
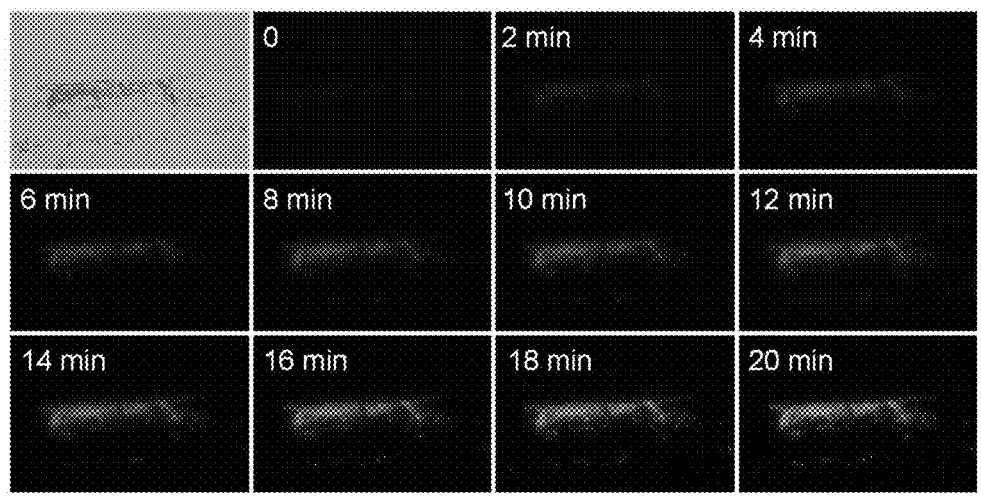
FIG. 13 shows a solid-state fluorescence photo of compound III-1 (i.e., method 1-compound III-1 in Example 2) under the irradiation of 365 nm ultraviolet light with elapse of time.
Figure 14:
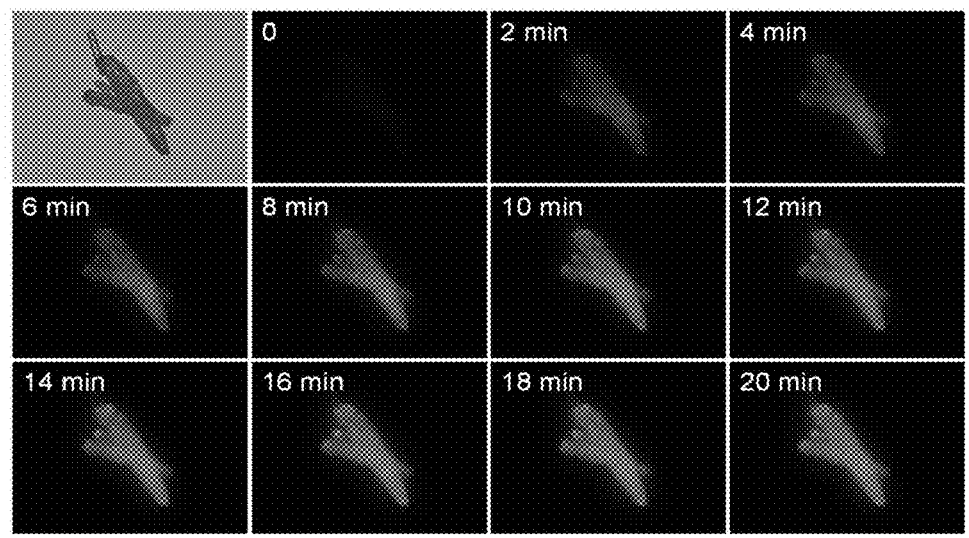
FIG. 14 shows a solid-state fluorescence photo of compound III-2 (i.e., method 1-compound III-2 in Example 2) under the irradiation of 365 nm ultraviolet light with elapse of time.
Figure 15:
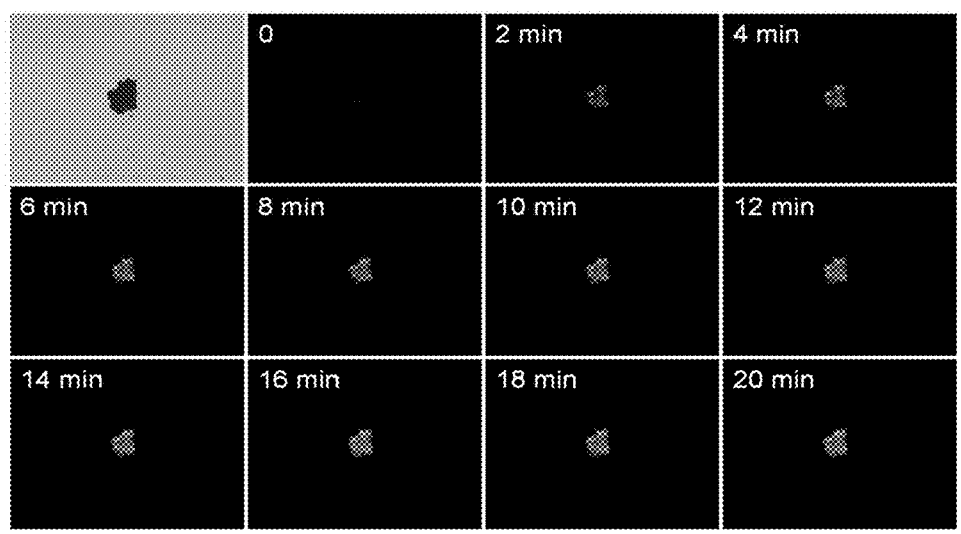
FIG. 15 shows a solid-state fluorescence photo of compound III-3 (i.e., method 1-compound III-3 in Example 2) under the irradiation of 365 nm ultraviolet light with elapse of time.

In the solid state under the irradiation of a 365 nm UV lamp, compounds III-1 to III-3 (i.e., method 1-compound III-1 to method 1-compound III-3 in Example 2) increased continuously in the fluorescence intensity with the irradiation time (see FIGS. 13-15), which was because compound III could also generate compound IV through photo-oxidative dehydrogenation reaction in the solid state. FIG. 13 shows a solid-state fluorescence photo of compound III-1 (i.e., method 1-compound III-1 in Example 2) under the irradiation of 365 nm ultraviolet light with elapse of time. FIG. 14 shows a solid-state fluorescence photo of compound III-2 (i.e., method 1-compound III-2 in Example 2) under the irradiation of 365 nm ultraviolet light with elapse of time. FIG. 15 shows a solid-state fluorescence photo of compound III-3 (i.e., method 1-compound III-3 in Example 2) under the irradiation of 365 nm ultraviolet light with elapse of time.

Example 11

Figure 16:
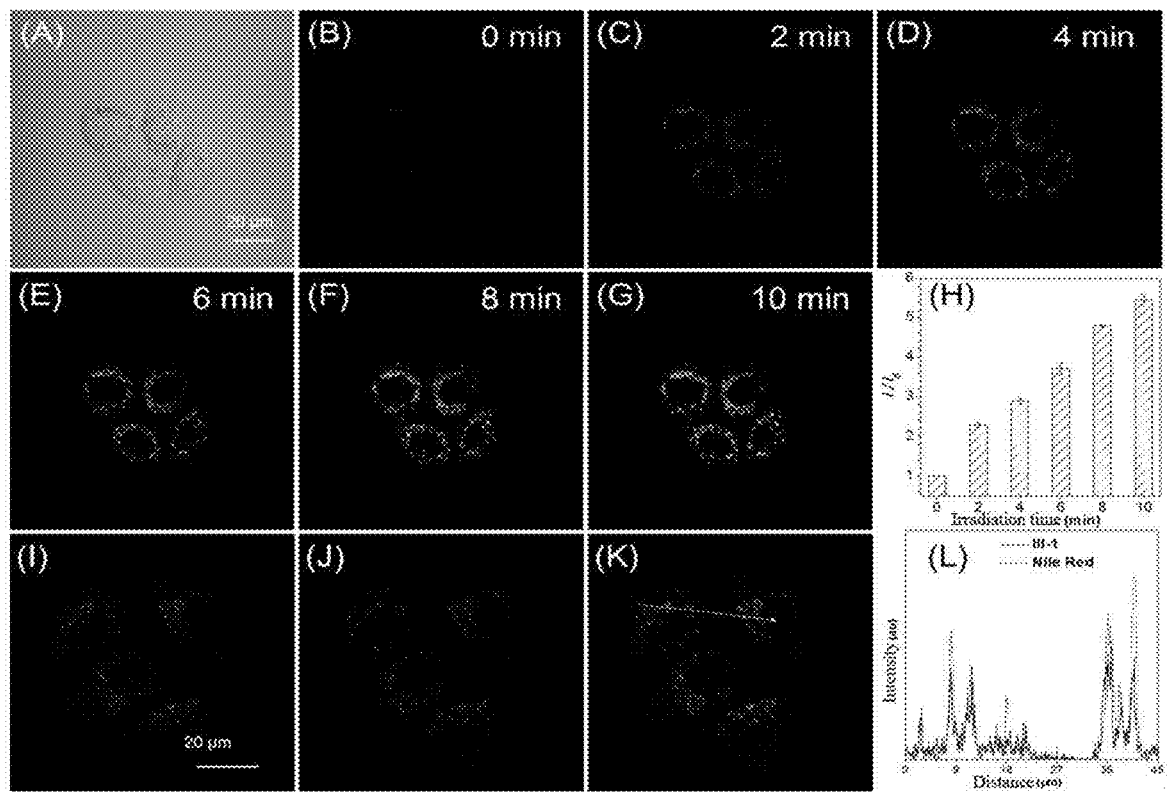
In FIG. 16: (A) the bright field of HeLa cells; (B-G) confocal fluorescence photos of the in-situ generated compound III-1 in HeLa cells under the irradiation of 405 nm laser that change with the scanning time; (H) the statistical change in fluorescence intensity; (I) the fluorescence dyeing of the photo-activatable compound 11I-1 in HeLa cells; (J) the fluorescence dyeing of the lipid droplet dye Nile Red in HeLa cells; (K) an overlay of (I) and (J); and (L) the change in the fluorescence signal of the photo-activatable compound 111-1 and Nile Red in a selected region.
Figure 17:
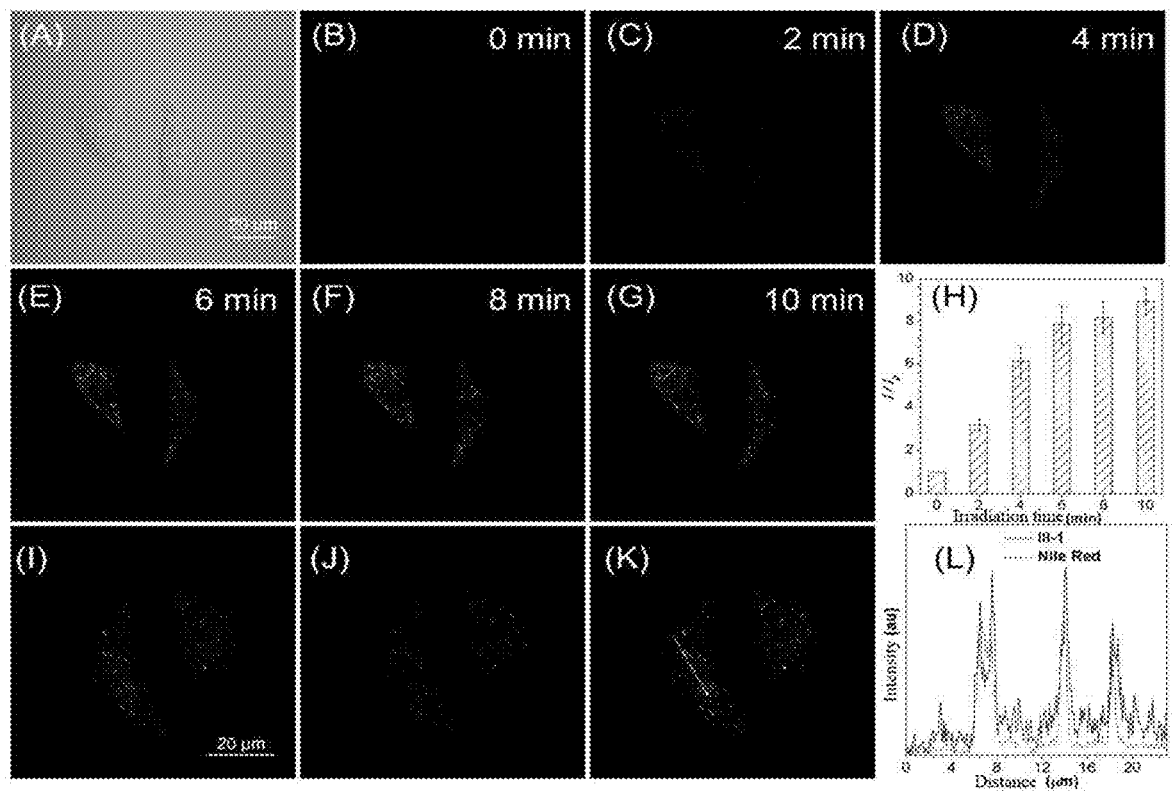
In FIG. 17: (A) the bright field of MCF-7 cells; (B-G) confocal fluorescence photos of the in-situ generated compound III-1 in MCF-7 cells under the irradiation of 405 nm laser that change with the scanning time; (H) the statistical change in fluorescence intensity; (1) the fluorescence dyeing of the photo-activatable compound III-1 in MCF-7 cells; (J) the fluorescence dyeing of the lipid droplet dye Nile Red in MCF-7 cells; (K) an overlay of (1) and (J); and (L) the change in the fluorescence signal of the photo-activatable compound 111-1 and Nile Red in a selected region.

Application of In-Situ Generated Compounds III-1 to III-3 in Photo-Activatable Fluorescence Imaging:

Compound III-1 was prepared in situ by mixing compound I-1 (10.0 mM, 100 μL) with a dimethyl sulfoxide solution of ethyl mercaptoacetate (20.0 mM, 100 μL), then 5.0 μL of this mixed solution was added to an HBSS buffer solution (1.0 ml) containing cells; in-situ generated compound III-1 did not emit fluorescence in HeLa cells or MCF-7 cells (the cells were purchased from ATCC company of the United States) at first, but increased rapidly in fluorescence emission intensity under the irradiation of 405 nm laser; when the irradiation time was increased to 10 min, the fluorescence intensity in HeLa cells and MCF-7 cells increased to approximately 5.5 times and 9.0 times of the initial value, respectively, indicating that the in-situ generated compound III-1 had a high photo-activation efficiency. It was shown by the co-dyeing experiments with the commercial lipid droplet dye Nile Red that compound III-1 could be used for lipid droplet specific photo-activatable fluorescence imaging (see FIGS. 16-17).

Figure 18:
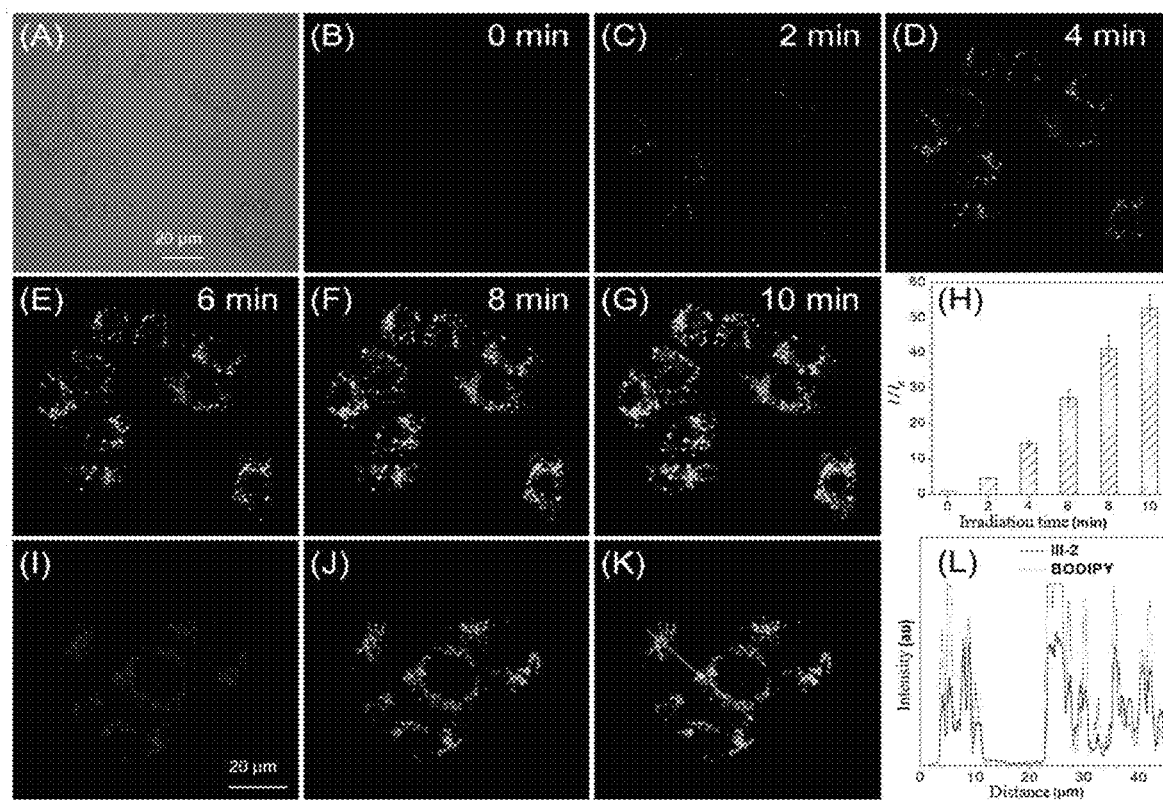
In FIG. 18: (A) the bright field of HeLa cells; (B-G) confocal fluorescence photos of the in-situ generated compound III-2 in HeLa cells under the irradiation of 405 nm laser that change with the scanning time; (H) the statistical change in fluorescence intensity; (1) the fluorescence dyeing of the photo-activatable compound III-2 in HeLa cells; (J) the fluorescence dyeing of the lipid droplet dye BODIPY493/503 Green in HeLa cells; (K) an overlay of (I) and (J); and (L) the change in the fluorescence signal of the photo-activatable compound 111-2 and BODIPY493/503 Green in a selected region.
Figure 19:
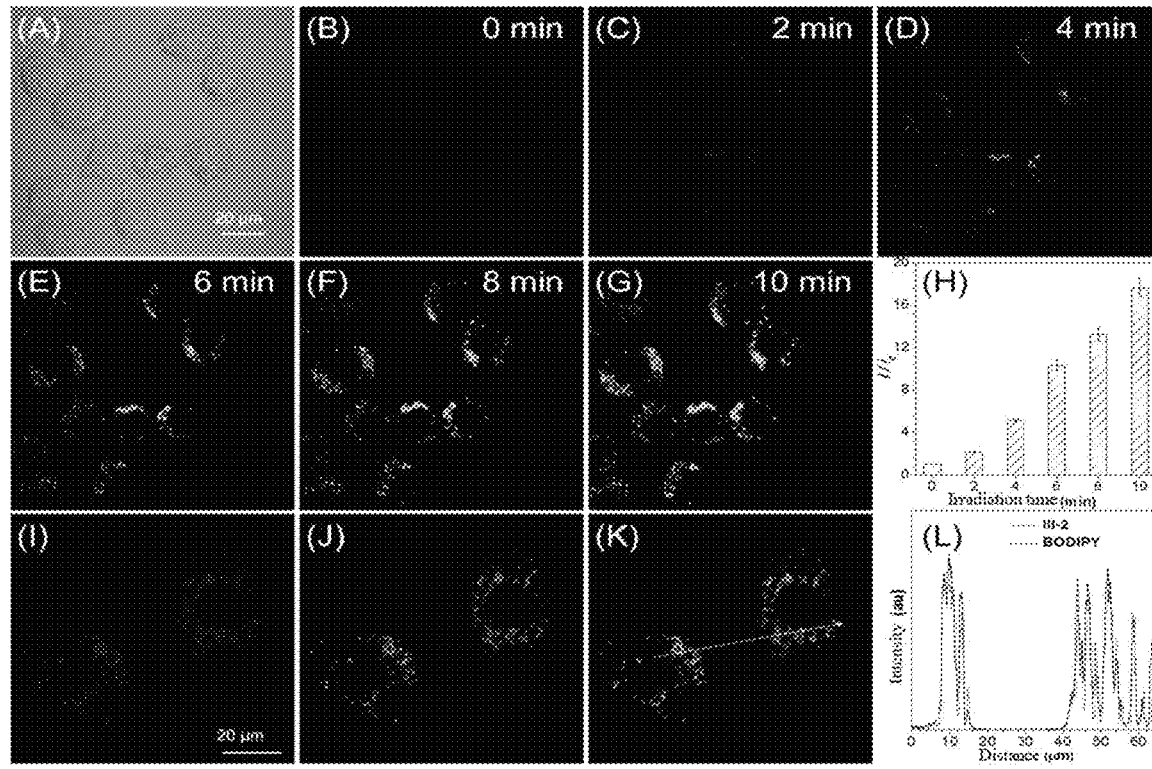
In FIG. 19: (A) the bright field of MCF-7 cells; (B-G) confocal fluorescence photos of the in-situ generated compound III-2 in MCF-7 cells under the irradiation of 405 nm laser that change with the scanning time; (H) the statistical change in fluorescence intensity; (I) the fluorescence dyeing of the photo-activatable compound III-2 in MCF-7 cells; (J) the fluorescence dyeing of the lipid droplet dye BODIPY493/503 Green in MCF-7 cells; (K) an overlay of (I) and (J); and (L) the change in the fluorescence signal of the photo-activatable compound III-2 and BODIPY493/503 Green in a selected region.

Compound III-2 was prepared in situ by mixing compound I-1 (10.0 mM, 100 μL) with a dimethyl sulfoxide solution of ethyl mercaptoacetate (20.0 mM, 100 μL), then 5.0 μL of this mixed solution was added to an HBSS buffer solution (1.0 mL) containing cells; in-situ generated compound III-2 did not emit fluorescence in HeLa cells or MCF-7 cells at first, but increased rapidly in fluorescence emission intensity under the irradiation of 405 nm laser; when the laser scanning time was increased to 10 min, the fluorescence intensity in HeLa cells and MCF-7 cells increased to approximately 53 times and 18 times of the initial value, respectively, indicating that the in-situ generated compound III-2 had a high photo-activation efficiency. It was shown by the co-dyeing experiments with the commercial lipid droplet dye BODIPY493/503 that compound III-2 could be used for lipid droplet specific photo-activatable fluorescence imaging (see FIGS. 18-19).

Figure 20:
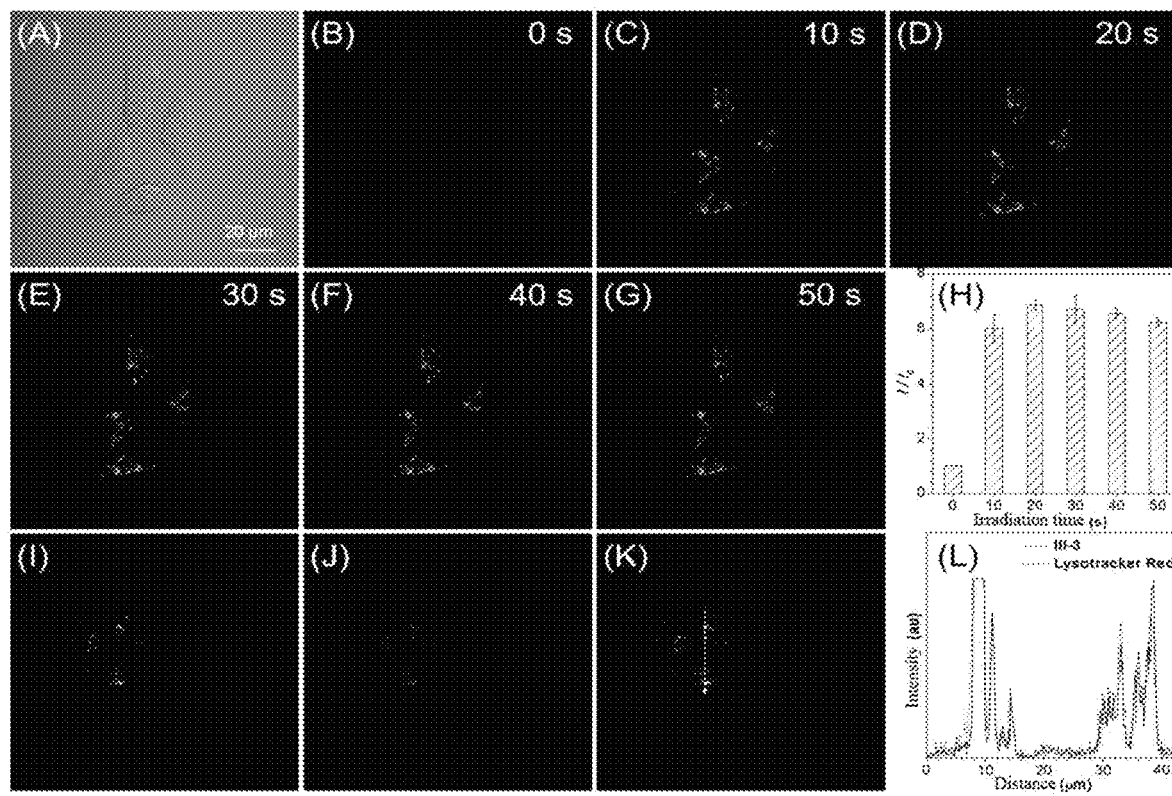
In FIG. 20: (A) the bright field of HeLa cells; (B-G) confocal fluorescence photos of the in-situ generated compound III-3 in HeLa cells under the irradiation of 405 nm laser that change with the scanning time; (H) the statistical change in fluorescence intensity; (I) the fluorescence dyeing of the photo-activatable compound III-3 in HeLa cells; (J) the fluorescence dyeing of the lysosomal dye LysoTracker Red in HeLa cells; (K) an overlay of (I) and (J); and (L) the change in the fluorescence signal of the photo-activatable compound III-3 and LysoTracker Red in a selected region.
Figure 21:
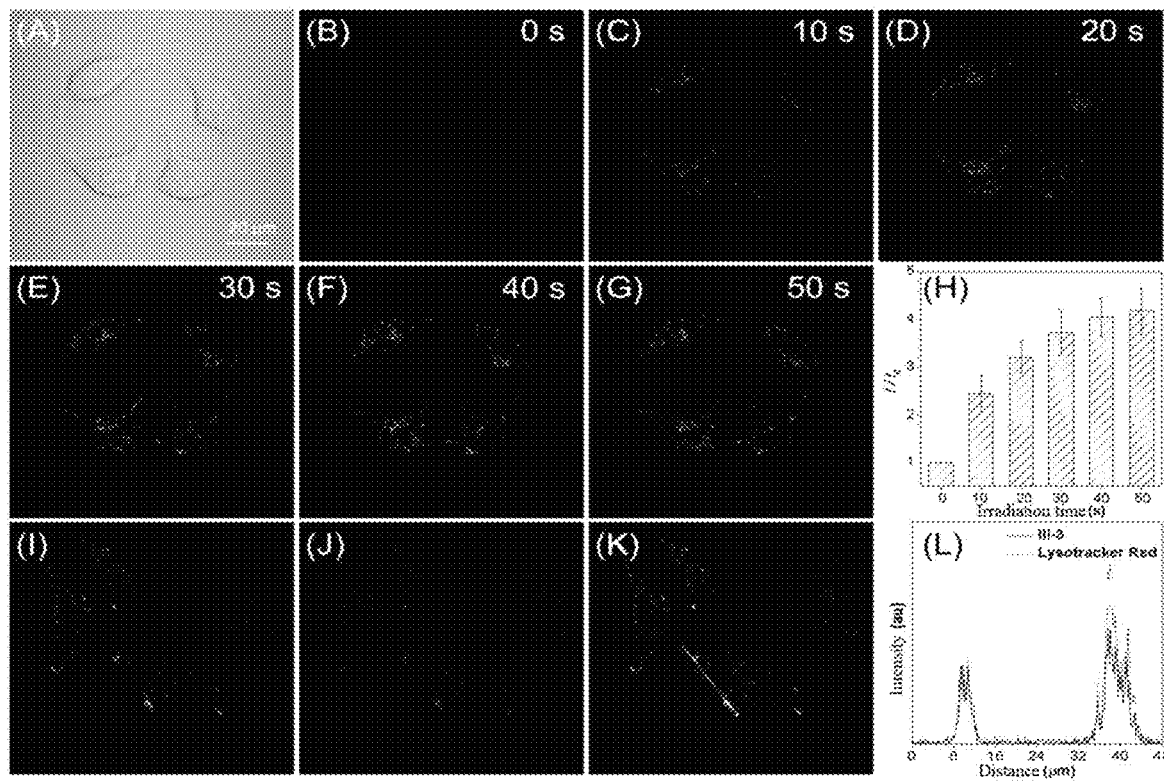
In FIG. 21: (A) the bright field of MCF-7 cells; (B-G) confocal fluorescence photos of the in-situ generated compound III-3 in MCF-7 cells under the irradiation of 405 nm laser that change with the scanning time; (H) the statistical change in fluorescence intensity; (1) the fluorescence dyeing of the photo-activatable compound III-3 in MCF-7 cells; (J) the fluorescence dyeing of the lysosomal dye LysoTracker Red in MCF-7 cells; (K) an overlay of (I) and (J); and (L) the change in the fluorescence signal of the photo-activatable compound III-3 and LysoTracker Red in a selected region.

Compound III-3 was prepared in situ by mixing compound I-3 (10.0 mM, 100 μL) with a dimethyl sulfoxide solution of ethyl mercaptoacetate (20.0 mM, 100 μL), then 2.0 μL of this mixed solution was added to an HBSS buffer solution (1.0 mL) containing cells; in-situ generated compound III-3 did not emit fluorescence in HeLa cells or MCF-7 cells at first, but increased rapidly in fluorescence intensity under the irradiation of 405 nm laser; when the laser scanning time was increased to 50 s, the fluorescence intensity in HeLa cells and MCF-7 cells increased to approximately 6.2 times and 4.5 times of the initial value, respectively, indicating that the in-situ generated compound III-3 had a high photo-activation efficiency. It was shown by the co-dyeing experiments with the commercial lysosomal dye LysoTracker Red that compound III-3 could be used for lysosomal specific photo-activatable fluorescence imaging (see FIGS. 20-21).

Example 12

Figure 22:
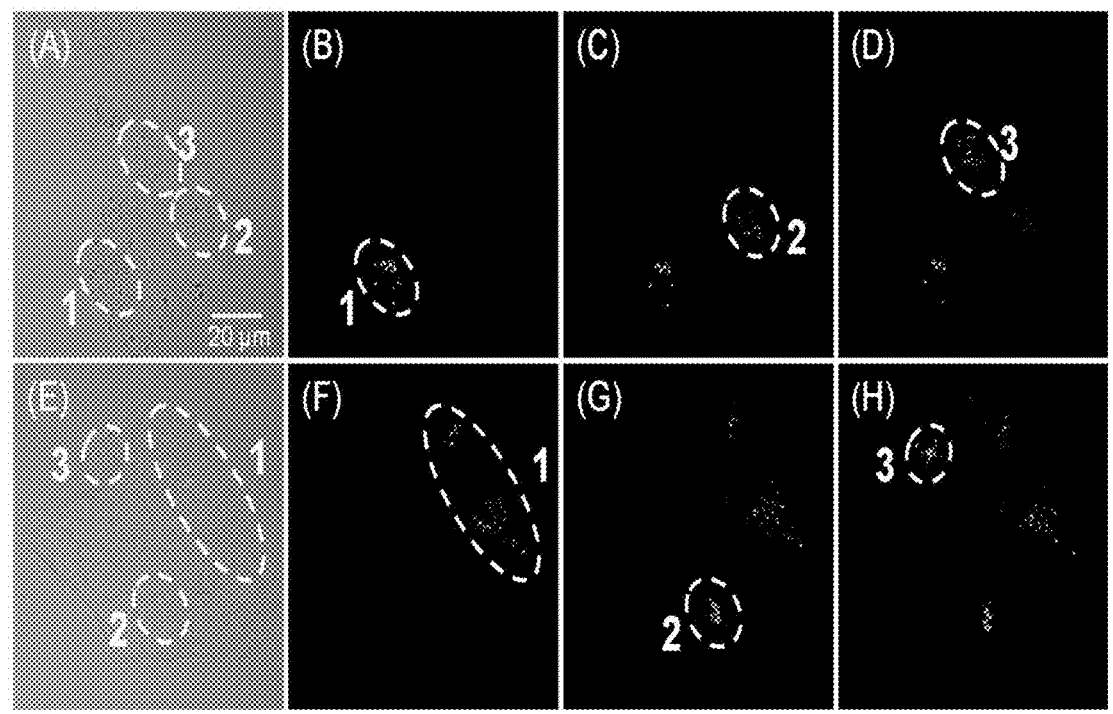
FIG. 22 shows, under the irradiation of 780 nm two-photon laser in the field of view of multiple HeLa cells: (A-D) the fluorescence of compound III-2 in the selected cells that is photo-activatable gradually in turn to achieve the photo-controlled lipid droplet high-spatiotemporal-resolution fluorescence imaging; and (E-H) the fluorescence of compound III-3 in the selected cells that is gradually photo-activatable in turn to achieve the photo-controlled lysosomal high-spatiotemporal-resolution fluorescence imaging.

In-situ generated compound III could be used for photo-controlled high-spatiotemporal-resolution imaging. Taking HeLa cells as an example, in a multicellular environment, under photo-control, compound III-2 could sequentially activate lipid droplets in different cells, and compound III-3 could sequentially activate lysosomes in different cells (see FIG. 22). The photo-controlled high-spatiotemporal-resolution imaging capability of in-situ generated compound III was particularly useful for monitoring the movement of organelles and studying the physiological functions of organelles in complex physiological environments.

The present invention established a method for efficiently generating 2-(2-hydroxyphenyl)benzothiazolines in situ, which could generate 2-(2-hydroxyphenyl)benzothiazoles with the aggregation-induced emission property through photo-activation. Due to limited movement in molecules and proton transfer mechanism in excited molecules, the 2-(2-hydroxyphenyl)benzothiazole compound did not emit fluorescence in the solution state or emitted very weak light, but emitted strong fluorescence in the aggregation state. The 2-(2-hydroxyphenyl)benzothiazoline compound generated in situ could be used as photo-activatable fluorescent probes for organelle-targeted photo-controlled high-spatiotemporal-resolution fluorescence imaging.

The above-described examples are preferred embodiments of the present invention, but the embodiments of the present invention are not limited thereto, and any other alterations, modifications, substitutions, combinations and simplifications should be equivalent replacements and included in the scope of protection of the present invention.

The invention claimed is:

1. A method of preparing a photo-activatable aggregation-induced emission probe with in-situ generation capability, wherein the method comprises obtaining the photo-activatable aggregation-induced emission probe by reacting a compound of formula I with a thiol; wherein:

the structure of the photo-activatable aggregation-induced emission probe is as shown in formula III:

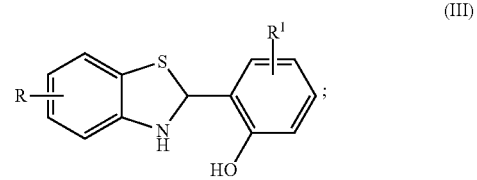

the compound of formula I is a bis(2-(2-hydroxybenzylidene)amino)aryl disulfide compound, having a structure as shown in the following formula I:

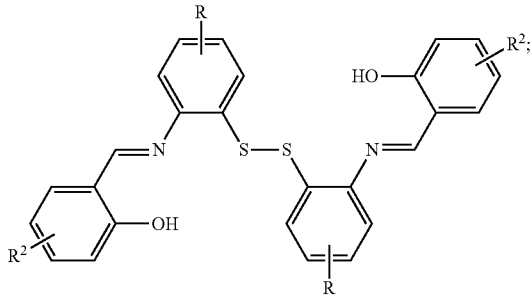

the thiol is a mercapto-containing amino acid, a mercapto-containing polypeptide, or has a structure as shown in formula II:

in formulas I and III, R and $R^1$ are independently hydrogen, halogen, ester group, cyano group, nitro group, substituted or unsubstituted alkyl, alkoxy, alkylamino group, alkylthio group, aryl, heteroaryl, aryloxy, arylamino group, arylthio group, heteroaryloxy, heteroarylamino group, or heteroarylthio group; and $R^2$ is a substituted or unsubstituted alkyl or a substituted or unsubstituted aryl; the substituted alkyl is hydroxyl substituted alkyl, ester-group substituted alkyl, or carboxyl substituted alkyl; the hydroxyl substituted alkyl is an alkyl on which hydrogen is replaced by a hydroxyl; the ester-group substituted alkyl is an alkyl on which carbon is replaced by an ester group; and the carboxyl substituted alkyl is an alkyl on which carbon is replaced by a carboxyl.

2. The method of preparing the photo-activatable aggregation-induced emission probe with in-situ generation capability according to claim 1, wherein:
in formulas I and III, the substituted alkyl means that hydrogen in the alkyl is replaced by a group formed by a cyclic compound, wherein the cyclic compound is a cyclic compound formed by carbon and hydrogen and one or more of heteroatoms N, S and O;
in formulas I and III, the substituted or unsubstituted alkyl is a $C_{1-30}$ alkyl, the alkoxy is a $C_{1-30}$ alkoxy, the alkylamino group is a $C_{1-30}$ alkylamino group, and the alkylthio group is a $C_{1-30}$ alkylthio group;
in formulas I and III, the aryl refers to a monocyclic or polycyclic aromatic group with 6-20 carbon atoms;
aryls in the aryloxy, arylamino group and arylthio group are each independently a monocyclic or polycyclic aromatic group with 6-20 carbon atoms;
the heteroaryl refers to a monocyclic or polycyclic heteroaromatic group with 1-20 carbon atoms and 1-4 heteroatoms selected from N, S and O;
heteroaryls in the heteroaryloxy, heteroarylamino group, and heteroarylthio group are each independently a monocyclic or polycyclic heteroaromatic group with 1-20 carbon atoms and 1-4 heteroatoms selected from N, S and O; and in formula II, $R^2$ is a substituted or unsubstituted $C_{1-30}$ alkyl.

3. The method of preparing the photo-activatable aggregation-induced emission probe with in-situ generation capability according to claim 1, wherein the method comprises carrying out the reacting of the compound of formula I with the thiol in one or more organic solvents; wherein:
the one or more organic solvents are selected from dimethyl sulfoxide, N,N-dimethylformamide, acetone, acetonitrile, dichloromethane, trichloromethane and tetrahydrofuran;
a reaction temperature is 15° C. to 40° C., and a reaction time is 1-30 min;
the thiol is a compound of formula II; and
the molar ratio of the compound of formula I to the compound of formula II is from 1:2 to 1:10.

4. The method of preparing the photo-activatable aggregation-induced emission probe with in-situ generation capability according to claim 1, wherein the compound of formula I is prepared through: dissolving a compound of formula V

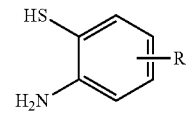

in an organic solvent and adding hydrogen peroxide at 20° C. to 60° C. to generate a compound of formula VI

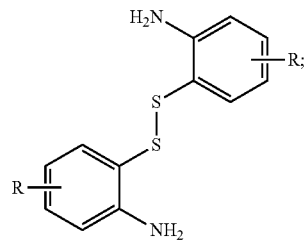

and reacting the compound of formula VI with a compound of formula VII

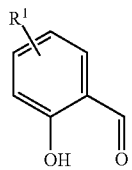

under reflux in an organic solvent to obtain the compound of formula I;
wherein in the compound of formula V, the compound of formula VI and the compound of formula VII, the definitions of the substituents R and $R^1$ are the same as in the compound of formula I.

* * * * *